US006008202A

United States Patent [19]
Huang et al.

[11] Patent Number: 6,008,202
[45] Date of Patent: Dec. 28, 1999

[54] STABLE LIPID-COMPRISING DRUG DELIVERY COMPLEXES AND METHODS FOR THEIR PRODUCTION

[75] Inventors: Leaf Huang, Wexford, Pa.; Xiang Gao, Nashville, Tenn.; Frank L. Sorgi, Sonoma, Calif.; Ralph Wilfred Paul, Seattle, Wash.; David L. Sloane, Bainbridge Island, Wash.; Aaron Garth Loomis, Seattle, Wash.

[73] Assignees: University of Pittsburgh; Targeted Genetics Corporation

[21] Appl. No.: 08/939,874

[22] Filed: Sep. 29, 1997

Related U.S. Application Data

[63] Continuation-in-part of application No. 08/751,888, Nov. 18, 1996, abandoned, and a continuation-in-part of application No. 08/376,701, Jan. 23, 1995, Pat. No. 5,795,587.

[51] Int. Cl.$^6$ .......................... A61K 9/127; A61K 31/00; A61K 48/00
[52] U.S. Cl. .................................. 514/44; 514/1; 424/450
[58] Field of Search ................................. 424/450; 514/1, 514/44

[56] References Cited

U.S. PATENT DOCUMENTS

| | | | |
|---|---|---|---|
| 4,544,545 | 10/1985 | Ryan et al. | 424/1.21 |
| 4,897,355 | 1/1990 | Eppstein et al. | 424/450 |
| 4,958,013 | 9/1990 | Letsinger | 536/24.5 |
| 5,100,662 | 3/1992 | Bolcsak et al. | 424/450 |
| 5,264,618 | 11/1993 | Felgner et al. | 560/224 |
| 5,279,833 | 1/1994 | Rose | 424/450 |
| 5,283,185 | 2/1994 | Epand et al. | 435/458 |
| 5,334,761 | 8/1994 | Gebeyehu et al. | 564/197 |
| 5,366,737 | 11/1994 | Eppstein et al. | 424/450 |
| 5,374,548 | 12/1994 | Caras | 424/450 |
| 5,523,222 | 6/1996 | Page et al. | 435/172.3 |
| 5,540,933 | 7/1996 | Ruoslahti | 424/450 |
| 5,545,412 | 8/1996 | Eppstein et al. | 424/450 |
| 5,661,025 | 8/1997 | Szoka, Jr. et al. | 435/458 |
| 5,795,587 | 8/1998 | Gao et al. | 424/450 |

OTHER PUBLICATIONS

X Gao et al (1991) Biochem Biophys Res. Comm. 79:280–285.
Behr et al., "Efficient gene transfer into mammalian primary endocrine cells with lipolyamine–coated DNA" *Proc. Natl. Acad. Sci. USA* (1989) 86:6982–6986.
Cheetham et al., "Cholesterol sulfate inhibits the fusion of sendai virus to biological and model membranes" *J. Biol. Chem.* (1990) 265:12404–12409.
Demeneix, "Temporal and spatial expression of lipospermine–compacted genes transferred into chick embryos in vivo" *Bio Techniques* (1994) 16:496–501.
Felgner, "Lipofection: A highly efficient, lipid–mediated DNA–transfection procedure" *Proc. Natl. Acad. Sci. USA* (1987) 84:7413–7417.
Gao, X. and Huang, L., "A novel cationic liposome reagent for efficient transfection of mammalian cells" *Biochem. Biophys. Res. Comm.* (1991) 179:280–285.
Hui et al., "Induction of alloreactive cytotoxic T lymphocytes by intra–splenic immunization with allogenic class I major histocompatibility complex DNA and DC–CHOL cationic liposomes" *J. Liposome Res.* (1994) 4:1077–1078.
Letsinger et al., "Cholesteryl–conjugated oligonucleotides: Synthesis, properties, and activity as inhibitors of replication of human immunodeficiency virus in cell structure" *Proc. Natl. Acad. Sci. USA* (1989) 86:6553–6556.
Malone et al., "Cationic liposome–mediated RNA transfection" *Proc. Natl. Acad. Sci. USA* (1989) 86:6077–6081.
Pinnaduwage et al., "Use of a quaternary ammonium detergent in liposome mediated DNA transfection of mouse L–cells" *Biochim. Biophys. Acta* (1989) 985:33–37.
Rose et al., "A new cationic liposome reagent mediating nearly quantitative transfection of animal cells" *BioTechniques* (1991) 10:520–525.
Stamatatos et al., "Interactions of cationic lipid vesicles with negatively charged phospholipid vesicles and biological membranes" *Biochemistry* (1988) 27:3917–3925.
Sternberg et al., "New structures in complex formation between DNA and cationic liposomes visualized by freeze–fracture electron microscopy" *FEBS Lett.* (1994) 356:361–366.
Stewart et al., "Gene transfer in vivo with DNA–liposome complexes: Safety and acute toxicity in mice" *Human Gene Therapy* (1992) 3:267–275.
Zhou et al., "Lipophilic polylysines mediate efficient DNA transfection in mammalian cells" *Biochim. Biophys. Acta* (1991) 1065:8–14.

*Primary Examiner*—Bruce R. Campell
*Attorney, Agent, or Firm*—Morrison & Foerster LLP

[57] ABSTRACT

Novel stable, concentrated, biologically active and ready-to-use lipid-comprising drug delivery complexes and methods for their production are described. The biological activity of the complexes produced are comparable to the formulations prepared according to the prior art admixture method and upon purification, the complexes produced by the method of this invention are 50 to 500 fold more concentrated than the complexes formed by admixture. The method described herein provides for the large scale production of lipid-comprising drug delivery systems useful for gene therapy and other applications.

46 Claims, 28 Drawing Sheets

Average Particle Sizes (nm) With Matrix of Lipid:Protamine Sulfate:DNA Ratios

| Protamine Sulfate:DNA Ratio | Lipid:DNA Ratio | | | | | | |
|---|---|---|---|---|---|---|---|
| | 1:1 | 2:1 | 3:1 | 5:1 | 10:1 | | |
| 0:0 | 250<br>250 | 250<br>240 | 250<br>240 | 250<br>240 | 250<br>240 | Day 0<br>Day 7 | |
| 0:1 | 250<br>250 | 250<br>240 | 240<br>240 | 240<br>250 | 3,500<br>1,200 | Day 0<br>Day 7 | |
| 0.1:1 | 240<br>240 | 250<br>240 | 240<br>240 | 290<br>290 | 1,400<br>916 | Day 0<br>Day 7 | |
| 0.3:1 | 250<br>250 | 250<br>250 | 290<br>303 | 1,500<br>1,500 | 460<br>390 | Day 0<br>Day 7 | |
| 0.5:1 | 260<br>260 | 360<br>380 | 1,000<br>940 | 330<br>310 | 260<br>260 | Day 0<br>Day 7 | |
| 0.7:1 | 1,200<br>1,570 | 370<br>360 | 330<br>320 | 290<br>270 | 240<br>240 | Day 0<br>Day 7 | |
| 0.8:1 | 150<br>1,900 | 250<br>1,900 | 380<br>450 | 240<br>232 | 310<br>300 | Day 0<br>Day 7 | |
| 1.0:1 | 170<br>170 | 180<br>180 | 180<br>180 | 200<br>190 | 200<br>200 | Day 0<br>Day 7 | |
| 2.0:1 | 180<br>180 | 180<br>170 | 190<br>190 | 200<br>190 | 190<br>190 | Day 0<br>Day 7 | |
| 4.0:1 | 220<br>220 | 220<br>220 | 220<br>220 | 230<br>230 | 220<br>220 | Day 0<br>Day 7 | |

FIG. 20

STABLE LIPID-COMPRISING DRUG DELIVERY COMPLEXES AND METHODS FOR THEIR PRODUCTION

CROSS REFERENCE TO RELATED APPLICATIONS

This application is a continuation-in-part of U.S. patent application Ser. No. 08/751,888, filed on Nov. 18, 1996, now abandoned, and a continuation-in-part of U.S. patent application Ser. No. 08/376,701, filed on Jan. 23, 1995, now U.S. Pat. No. 5,795,587, issued Aug. 18, 1998, the disclosures of each of which are hereby incorporated by reference.

FIELD OF INVENTION

The present invention relates to cationic lipids and their use as vehicles for the transfer of nucleic acids or other macromolecules, such as proteins, into cells. More specifically, this invention relates to lipid-comprising drug delivery complexes which are stable, biologically active, capable of being concentrated, and to methods for their production.

BACKGROUND OF INVENTION

The development of new forms of therapeutics which use macromolecules such as proteins or nucleic acids as therapeutic agents has created a need to develop new and effective means of delivering such macromolecules to their appropriate cellular targets. Therapeutics based on either the use of specific polypeptide growth factors or specific genes to replace or supplement absent or defective genes are examples of therapeutics which may require such new delivery systems. Clinical application of such therapies depends not only on the efficacy of new delivery systems but also on their safety and on the ease with which the technologies underlying these systems can be adapted for large scale pharmaceutical production, storage, and distribution of the therapeutic formulations. Gene therapy has become an increasingly important mode of treating various genetic disorders. The potential for providing effective treatments, and even cures, has stimulated an intense effort to apply this technology to diseases for which there have been no effective treatments. Recent progress in this area has indicated that gene therapy may have a significant impact not only on the treatment of single gene disorders, but also on other more complex diseases such as cancer. However, a significant obstacle in the attainment of efficient gene therapy has been the difficulty of designing new and effective means of delivering therapeutic nucleic acids to cell targets. Thus, an ideal vehicle for the delivery of exogenous genes into cells and tissues should be highly efficient in nucleic acid delivery, safe to use, easy to produce in large quantity and have sufficient stability to be practicable as a pharmaceutical.

Non-viral vehicles, which are represented mainly by the cationic liposomes, are one type of vehicle which have, for the following reasons, been considered for use in gene therapy. First, the plasmid DNA required for liposome-mediated gene therapy can be widely and routinely prepared on a large scale and is simpler and carries less risk than the use of viral vectors such as retroviruses. Second, liposome-mediated gene delivery, unlike retroviral-mediated gene delivery, can deliver either RNA or DNA. Thus, DNA, RNA, or an oligonucleotide can be introduced directly into the cell. Moreover, cationic liposomes are non-toxic, non-immunogenic and can therefore be used repeatedly in vivo as evidenced by the successful in vivo delivery of genes to catheterized blood vessels (Nabel, E. G., et al. (1990) *Science*, 249: 1285–1288), lung epithelial cells (Brigham, K. L., et al. (1989) *Am. J. Respir. Cell Mol. Biol.*, 195–200, Stribling, R., et al. (1992) *Proc. Natl. Acad. Sci. U.S.A.*, 89: 11277–11281), and other systemic uses (Zhu, N., et al. (1993) *Science*, 261: 209–211, Philip, R., et al. (1993) *Science*, 261: 209–211; Nabel, G. et al (1994) *Hum. Gene Ther.*, 5:57–77) of cationic liposomes.

Although a variety of cationic liposome formulations, including the commercially available cationic liposome reagent DOTMA/DOPE (N-1, -(2,3-dioleoyloxy) propyl-N, N,N-trimethyl ammonium chloride/dioleoyl phosphatidylethanolamine), are known in the art (Felgner, P. L. et al. (1987) *Proc. Natl. Acad. Sci. U.S.A.*, 84: 7413–7417), a cationic liposome formulation designated DC-Chol/DOPE (3βN-(N',N'-dimethylaminoethane)-carbamoyl cholesterol/(dioleoyl phosphatidylethanolamine) has been shown in in vitro studies (Gao, X., and Huang, L. (1991) *Biochem. Biophys. Res. Commun.*, 179: 280–285) to be relatively nontoxic and more efficient than DOTMA/DOPE. Moreover, following extensive in vivo studies (Plautz, G. E., et al. (1993) *Proc. Natl. Acad. Sci. U.S.A.*, 90: 4645–4649, Stewart, M. J., et al. (1992) *Hum. Gene Ther.*, 3: 267–275) in which DC-Chol/DOPE was demonstrated to be both safe and efficacious as a nucleic acid delivery system, this formulation was approved by the U.S. Food and Drug Administration (FDA) and the U.K. Medicines Control Agency (MCA), and has been used in two separate gene therapy clinical trials (Nabel, G. J., et al. (1993) *Proc. Natl. Acad. Sci. U.S.A.*, 90: 11307–11311, Caplen, N. J., et al. (1995) *Nature Medicine*, 1: 39–46).

However, the use of DC-Chol/DOPE and other currently existing cationic liposomes as vehicles for delivering nucleic acids to cellular targets are inconvenient for large scale therapeutic applications for a number of reasons. First, the ratios of liposome to nucleic acid utilized to form nucleic acid/liposome complex in the prior art admixture method results in the formation of complexes which are large in diameter and relatively unstable. Thus, none of the presently utilized cationic liposome formulations, including DC-Chol/DOPE, are designed as stable and ready-to-use pharmaceutical formulations of nucleic acid/liposome complex. This limitation of the admixture method requires that the user prepare the complex prior to each use, an inconvenience which requires special training of personnel. In addition, the preparation of the complex by admixture prior to each use introduces a possible source of dosage variability which hinders evaluation of treatments utilizing these complexes due to possible over- or under-dosing of the recipient.

Second, the prior art admixture method of preparing nucleic acid/cationic liposome complexes prior to each use requires that a dilute nucleic acid solution (less than 4 μg/ml) and a dilute liposome dispersion (less than 50 μM) be used to prepare the nucleic acid/liposome complex in order to reduce the chance of forming large and less active aggregates. This limitation makes it difficult to make small biologically active complexes without using less than optimal conditions, such as reducing the amount of liposomes (which causes reduced nucleic acid transfer activity) or increasing the amount of liposome (which causes enhanced toxicity). Moreover, the fact that the complex must be made in dilute concentrations is a significant drawback to clinical applications, particularly in the case of intratumor injection of the complex, since only a small volume of the complex can be injected in each site (Nabel, G. J., et al. (1993) *Proc. Natl. Acad. Sci. U.S.A.*, 90: 11307–11311).

Accordingly, an object of this invention is to provide stable, biologically active, lipid-comprising drug delivery complexes which are capable of being formulated in a high concentration as well as methods of producing such complexes.

SUMMARY OF INVENTION

This invention provides methods for producing lipid-comprising drug delivery complexes having a net positive charge and/or a positively charged surface. By "drug" as used throughout the specification and claims is meant any molecular entity, which is either monomeric or oligomeric, and which, when complexed with lipid or with lipid and polycation, is being administered to an individual for the purpose of providing a therapeutic effect to the recipient. Thus, macromolecules having an overall net negative charge or regions of negativity would be expected to be capable of forming the delivery complexes of this invention. Macromolecules which are particularly suitable for use with the complexes of this invention are for example, DNA, RNA, oligonucleotides or negatively charged proteins. However, macromolecules having a positive charge (e.g., large cationic protein) would also be expected to be capable of forming the complexes of this invention by sequentially complexing the cationic macromolecule with anionic molecule or polymer and then with cationic lipid.

The complexes of the invention comprise a drug/lipid complex formed by mixing the drug to be delivered with cationic liposomes in a drug to lipid ratio such that the drug/lipid complex formed has a net positive charge and a drug/lipid/polycation complex formed by mixing drug with cationic liposomes and polycation in a drug to lipid to polycation ratio such that the drug/lipid/polycation complex formed has a net positive charge. By "net positive charge" as applied to the drug/lipid complex is meant a positive charge excess of lipid to drug. By "net positive charge" as applied to the drug/lipid/polycation complex is meant that the positive charges of the cationic lipid and the polycation exceed the negative charge of the drug. However, it is to be understood that the present invention also encompasses drug/lipid and drug/lipid/polycation complexes having a positively charged surface irrespective of whether the net charge of the complex is positive, neutral or even negative. A positively charged surface of a complex may be measured by the migration of the complex in an electric field by methods known to those in the art such as by measuring zeta potential (Martin, A., Swarick, J., and Cammarata, A., Physical Pharmacy & Physical Chemical Principles in the Pharmaceutical Sciences, 3rd ed. Lea and Febiger, Philadelphia, 1983), or by the binding affinity of the complex to cell surfaces. Complexes exhibiting a positively charged surface have a greater binding affinity to cell surfaces than complexes having a neutral or negatively charged surface. Furthermore, the positively charged surface could be sterically shielded by the addition of non-ionic polar compounds, of which polyethylene glycol is an example.

The invention therefore relates to methods for producing these drug/lipid and drug/lipid/polycation complexes comprising mixing the drug to be delivered with cationic liposomes, and optionally polycation, in a ratio such that the complex formed has a net positive charge and/or a positively charged surface.

In another embodiment of this invention, the methods for producing drug lipid or drug/lipid/polycation complexes may further comprise the step of purifying said complexes from excess free components (drug, lipid, polycation) following their production.

The drug/lipid and drug/lipid/polycation complexes of this invention are generally stable, capable of being produced at relatively high concentration, and retain biological activity over time in storage. Such complexes are of utility in the delivery of nucleic acids, proteins and other macromolecules to cells and tissues.

In another embodiment of this invention complexes are found comprising polycationic polypeptides having a high arginine content.

DESCRIPTION OF FIGURES

FIGS. 2A and 2B is indicated at the top of FIG. 2A.

FIG. 2A shows the distribution of the $^3$H and $^{32}$P markers following ultracentrifugation of free liposomes (10 $\mu$moles of DC-Chol/DOPE (2:3) in 2 ml volume) or free DNA (50 $\mu$g pRSVL DNA in a 2 ml volume) through a sucrose density gradient. FIG. 2B shows the distribution of the $^3$H and $^{32}$P markers following ultracentrifngation of the DNA-lipid complex (formed via mixing of 20 pmoles DC-Chol/DOPE (2:3) liposomes and 0.4 mg pRSVL DNA in 2 ml volume) through a sucrose density gradient.

FIG. 20 shows the relationship between Lipid:Protamine Sulfate:DNA ratios and particle sizes. The X axis describes the Protamine Sulfate:DNA ratio. The Y axis describes the Lipid:DNA ratio. Particle sizes (nm) corresponding to the respective ratios at Day 0 and Day 7 appear in the matrix cell at the intersection of the X and Y axes. Particle sizes around 200 nm are thought to be favorable since this represents optimal sizing for coated pit internalization.

DESCRIPTION OF INVENTION

Figure 1:
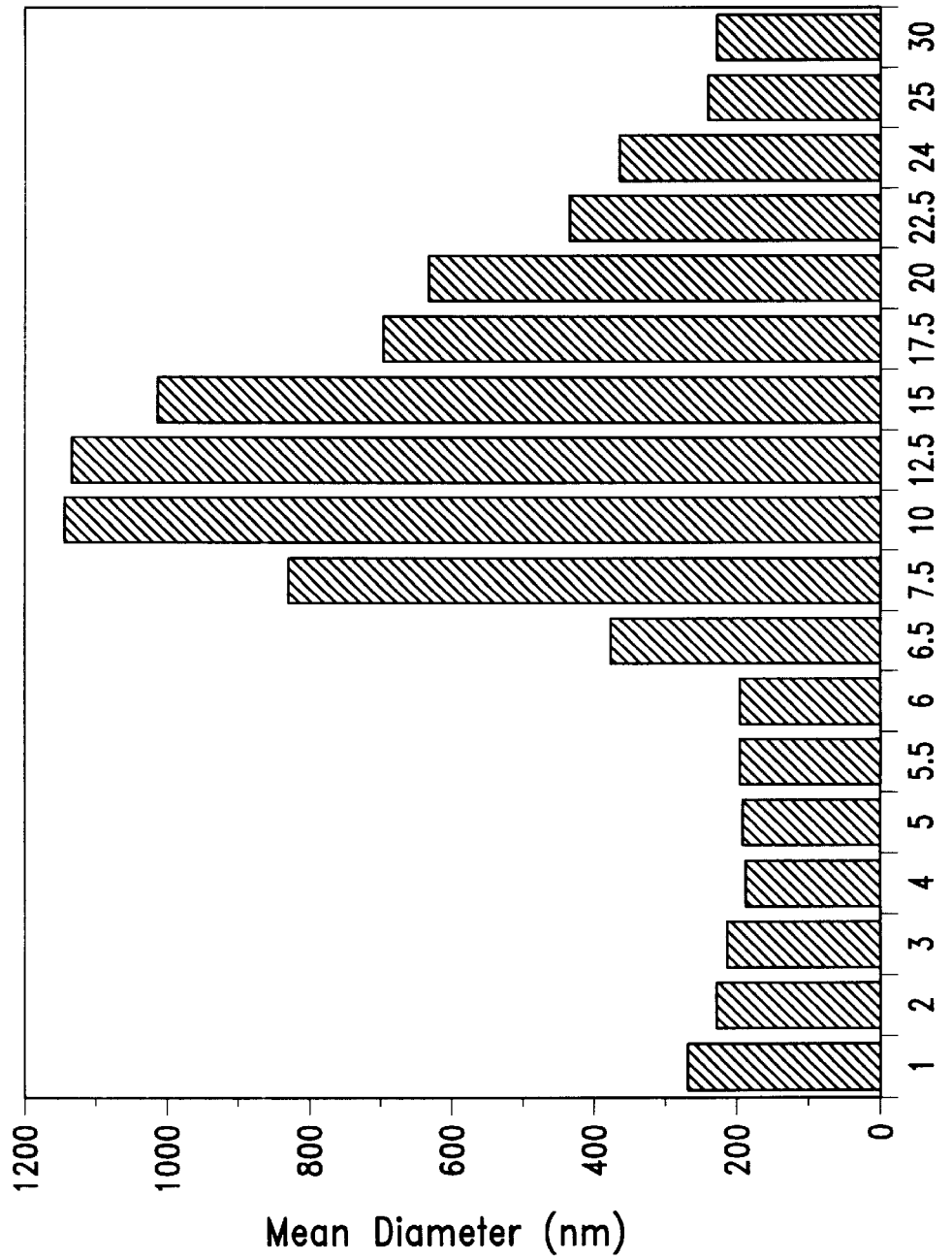
FIG. 1 shows a typical size distribution (mean diameter) of nucleic acid/liposome complexes prepared as an admixture from DC-Chol/DOPE (3:2 mol/mol) liposomes and pRSVL plasmid DNA (2 $\mu$g) at the indicated lipid to DNA ratios.

This invention relates to lipid-comprising drug delivery complexes having a net positive charge and/or a positively charged surface at pH 6.0–8.0. These complexes comprise lipids, drugs, and optionally further comprise polycations. The invention further relates to a method for producing these complexes where the method may optionally include the step of purifying these formulations from excess individual components. For the production of the drug/lipid complexes of this invention, inclusion of the purification step is a preferred embodiment. It should be understood that where the purification step is applied to the drug/lipid/polycation complexes, the recovery of these complexes in a pure state free from excess components following purification is lower than the recovery of drug/lipid complexes following their purification since the peak containing the drug/lipid/polycation complex following sucrose purification via density centrifugation is broader than the peak containing drug/lipid complexes and hence, overlaps with the peaks of the free components.

The lipid-comprising drug delivery complexes of this invention are stable, capable of being produced at relatively high concentrations, and retain biological activity of the drug component over time in storage. The method of producing these complexes is based on a binding model between two oppositely charged polymers (e.g. negatively charged nucleic acid and positively charged lipids) in which the formation of large unstable aggregates is avoided by neutralizing the negative charge of the drug via the use of an excess amount of positive charge in the form of cationic liposomes or cationic liposomes and polycation. The complexes of this invention have been observed to retain their initial diameter and bioactivity over 4 months in storage in 10% sucrose buffer.

The "drug" which is contained in the lipid-comprising drug delivery complexes of the present invention may be nucleic acids, polyanionic proteins, polysaccharides and other macromolecules which can be complexed directly with cationic lipids. However, cationic drugs (eg large cationic protein) can be directly complexed with an anionic lipid or sequentially complexed first with anionic lipid or polymer followed by cationic lipid. The use of this process permits delivery of positive or neutral charged drug to cells by the complexes of the present invention.

To produce drug/lipid and drug/lipid/polycation complexes with a net positive charge, the positive charge excess of lipid to drug or of lipid and polycation to drug may be up to about a 30-fold positive charge excess in the complex of total lipids to drug or of lipid and polycation to drug, preferably about a 2 to 10-fold charge excess and most preferably about a 2 to 6-fold charge excess. Complexes which possess a positive charge on their surface may have similar preferred ranges of surface charge excess to drug. To produce a nucleic acid/lipid complex having a positive charge excess of lipid to nucleic acid, mole amounts of cationic liposomal lipid to be mixed with 1 μg of nucleic acid to produce a nucleic acid/lipid complex which has positive charge excess of lipid to nucleic acid at pH 6.0–8.0 may range from about 0.1 nmol to about 200 nmol of lipid, preferably about 5 nmol to about 100 nmol lipid, depending on the positive charge content of the cationic liposome. Of course, if the drug were a protein, the amount of lipid to be mixed with 1 μg of negatively charged protein would be at least 10-fold less than the amount of lipid to be mixed with 1 μg of DNA as shown above since proteins are less charge dense than nucleic acids. Those of ordinary skill in the art would readily understand that depending upon the positive charge content of the cationic liposomes, different mole amounts of different cationic liposomes would have to be mixed with an equivalent amount of drug to produce a positive charge excess of lipid to drug.

When a drug/lipid/polycation complex having a net positive charge and/or a positively charged surface is to be produced, the inclusion of the polycation reduces the amount of lipid which must be mixed with drug to the extent that the positive charge from the lipid may be less than the negative charge from the drug. This reduction in the amount of lipid reduces the toxicity of the polycation-containing formulations. Mole amounts of cationic liposomes to be used in formulating nucleic acid/lipid/polycation complexes may range from about 0.1 nmol to about 200 nmol lipid per 1 μg nucleic acid, more preferably from about 1 to about 25 nmoles lipid per 1 μg nucleic acid depending on the positive charge content of the cationic liposomes. It is to be generally understood that in producing the nucleic acid/lipid and nucleic acid/lipid/polycation complexes of the present invention, the mole amount of liposomes required to produce these complexes will increase as the concentration of nucleic acid mixed with the liposomes is increased.

Those of ordinary skill in the art would readily understand that when the complexes of the present invention are purified, the positive charge excess of cationic liposomes to drug or of cationic liposomes and polycation to drug immediately prior to mixing will be greater than the positive charge excess in the purified complexes of lipid to drug or of lipid and polycation since the purification step results in the removal of excess free lipids and/or free polycation.

In order to illustrate how the charges attributed to cationic lipid, drug and polycation may be determined at pH 6.0–8.0 the following example is provided. Assuming the drug to be delivered is DNA, one determines the negative charge of the DNA to be delivered by dividing the amount of DNA to be mixed, or the amount of DNA in the complex, by 330, the molecular weight of a single nucleotide where one nucleotide equals one negative charge. Thus, the negative charge for 1 µg of DNA is 3.3 nmols.

For 10 nmol of DC-Chol/DOPE (2:3) liposomes one calculates the effective charge of the lipid by multiplying the amount of total liposomal lipid (10 nmol) by 0.4 (40% of the total liposomal lipid is the cationic lipid DC-Chol) to yield 4 nmol DC-Chol lipid in the liposomes. Since at pH 6–8, one molecule of DC-Chol has one positive charge, the effective positive charge of liposomal lipid at the time of mixing, or in the complex, is 4.0 nmol. Of course, those of skill in the art would readily understand that other cationic lipids may have a lesser or greater amount of positive charge per molecule of cationic lipid at pH 6–8.0 than DC-Chol.

Assuming the polycation to be mixed to form the complex is a bromine salt of poly-L-lysine (PLL), the positive charge of PLL at the time of mixing is obtained by dividing the amount of PLL to be mixed by 207, the molecular weight of one lysyl residue where one lysyl residue equals one positive charge. Thus, the positive charge for 1 µg of PLL is approximately 5.0 nmols. To calculate the positive charge contributed by lysyl residues in a formed complex, the amount of lysine present in the complex is divided by the molecular weight of one lysyl residue taking into account the weight of a counterion, if present.

Application of the above calculations to data presented in Table 1 herein (see Example 3) illustrates how a positive to negative charge ratio can be calculated both at the time of mixing of DNA and liposome and, after purification of the complex produced by the mixing of DNA and liposome. In Table 1 of Example 3, 0.4 mg of DNA is mixed with 20 µmols of cationic DC-Chol/DOPE liposomes to produce DNA/lipid complex. For cationic liposomes having a DC-Chol/DOPE ratio of 4:6, the positive charge content of the liposomal lipid is calculated to be 8000 nmol and the negative charge content of the 0.4 mg DNA to be mixed with liposomes is calculated to be 1320 nmols based on the sample calculations presented in the above paragraphs. Therefore, the positive to negative charge ratio at the time of mixing is 6.06 (8000 divided by 1320). However, after the complex was purified, the lipid to DNA ratio of this purified complex was 12.7 nmol lipid/µg DNA as shown in Table 1 (see the "4:6 row"). This 12.7 ratio translates to a positive to negative charge ratio of 1.5 thus showing that purification removed excess positive charge of free liposomes.

Also in Table 1, where DNA/lipid/PLL complex was prepared by mixing 4 µmol of liposomes (4:6 DC-Chol/DOPE) and 1 mg PLL with 0.4 mg DNA, one can calculate the positive to negative charge ratio at the time of mixing as follows. Based on the sample calculations presented in the above paragraphs, the 4 µmol liposomal lipid contributes 1600 nmol of positive charge, the 1 mg of PLL contributes 5000 µmol of positive charge and the 0.4 mg DNA contributes 1,320 nmol of negative charge. Thus, the positive to negative charge ratio at the time of mixing $$5\frac{(1600+5000)}{1320}.$$

It is further to be understood by those skilled in the art that the net charge of the complex may be determined by measuring the amount of DNA, lipid and when present, polycation in the complex by the use of an appropriate analytical technique such as the use of radioisotopic labelling of each component or by elemental analysis. Once the amounts of each component (DNA, lipid and when present, polycation) in a complex at a given pH are known, one could then calculate the approximate net charge of that complex at the given pH taking into account the pK's of the components which may be known or determined analytically.

In a preferred embodiment, the drug is a nucleic acid sequence, preferably a nucleic acid sequence encoding a gene product having therapeutic utility.

In one embodiment of the invention, a method for producing nucleic acid/lipid complexes having a net positive charge and/or positively charged surface at pH 6–8.0, comprises, combining nucleic acids with cationic liposomes in a nucleic acid to lipid ratio such that the nucleic acid/lipid complex formed has a positive charge excess of lipid to nucleic acid.

In an alternative embodiment, nucleic acid and cationic liposome may be mixed with a polycation in a nucleic acid to lipid to polycation ratio such that the nucleic acid/lipid/polycation complexes formed have a positive charge excess of lipid and polycation to nucleic acid at pH 6–8.

In a preferred embodiment, the nucleic acid/lipid and nucleic acid/lipid/polycation complexes are produced by slowly adding nucleic acid to the solution of liposome or liposome plus polycation and mixing with a stirring bar where the mixing is allowed to proceed second after addition of DNA. Alternatively, the liposome or liposome/polycation mix can be added into a single chamber from a first inlet at the same time the nucleic acid is added to the chamber through a second inlet. The components are then simultaneously mixed by mechanical means in a common chamber. The complexes may also be produced by first mixing the nucleic acid with the polycation and then adding the liposome suspension.

The cationic liposomes mixed with drug or with drug and polycation to form the complexes of the present invention may contain a cationic lipid alone or a cationic lipid in combination with a neutral lipid. Suitable cationic lipid species include, but are not limited to: 3β[$^4$N-($^1$N,$^8$N-diguanidino spermidine)-carbamoyl] cholesterol (BGSC); 3β[N,N-diguanidinoethyl-aminoethane)-carbamoyl] cholesterol (BGTC); N,N$^1$,N$^2$,N$^3$ Tetra-methyltetrapalmitylspermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2 (sperminecarboxamido)ethyl]-N,N-dimethyl-1-propanaminium trifluorocetate) (DOSPA); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N'-tetramethyl-N,N'-bis(2-hydroxyethyl)-2,3 dioleoyloxy-1,4-butanediammonium iodide) (Tfx-50); 1,2 bis(oleoyloxy)-3-(trimethylammonio) propane (DOTAP); N-1-(2,3-dioleoyloxy) propyl-N, N, N-trimethyl ammonium chloride (DOTMA) or other N-(N, N-1-dialkoxy)-alkyl-N, N, N-trisubstituted ammonium surfactants; 1,2 dioleoyl-3-

(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DORI (DL-1, 2-dioleoyl-3-dimethylaminopropyl-β-hydroxyethylammonium) or DORIE (DL-1, 2-O-dioleoyl-3-dimethylaminopropyl-β-hydroxyethylammonium) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES) or the cationic lipids disclosed in U.S. Pat. No. 5,283,185, cholesteryl-3β-carboxyl-amido-ethylenetrimethyl-ammonium iodide, 1-dimethylamino-3-trimethylammonio-DL-2-propyl-cholesteryl carboxylate iodide, cholesteryl-3β-carboxyamidoethyleneamine, cholesteryl-3β-oxysuccinamido-ethylenetrimethylammonium iodide, 1-dimethylamino-3-trimethylammonio-DL- 2-propyl-cholesteryl-3, β-oxysuccinate iodide, 2-(2-trimethylammonio)-ethylmethylamino ethyl-cholesteryl-3β-oxysuccinate iodide, 3βN-(N', N'-dimethylaminoethane) carbamoyl cholesterol (DC-chol), and 3β-N-(polyethyleneimine)-carbamoylcholesterol.

Examples of preferred cationic lipids include N-t-butyl-N'-tetradecyl-3-tetradecyl-aminopropion-amidine (CLONfectin), 2,3-dioleoyloxy-N-[2 (sperminecarboxamido)ethyl]-N,N-dimethyl-1-propanaminium trifluoroacetate (DOSPA), 1,2-bis (oleoyloxy)-3-(trimethylammonio)propane (DOTAP), N-[1-(2,3, dioleoyloxy)propyl]-N,N,N-trimethylammonium chloride) (DOTMA), cholesteryl-3β-carboxyamidoethylenetri-methylammonium iodide, 1-dimethylamino-3-trimethylammonio-DL-2-propyl-cholesteryl carboxylate iodide, cholesteryl-3β-carboxyamidoethyleneamine, cholesteryl-3β-oxysuccin-amidoethylenetrimethyl-ammonium iodide, 1-dimethylamino-3-trimethylammonio-DL-2-propyl-cholesteryl-3β-oxysuccinate iodide, 2-(2-trimethylammonio)ethylmethylamino ethyl-cholesteryl-3β-oxysuccinateiodide, 3βN-(N', N'dimethyl-aminoethane)-carbamoyl-cholesterol (DC-chol), and 3βN-(polyethyleneimine)-carbamoyl cholesterol.

Since an attribute of the complexes of the invention is their stability during storage (i.e., their ability to maintain a small diameter and retain biological activity over time following their formation); it will be understood by those of ordinary skill in the art that preferred cationic lipids are those lipids in which bonds between the lipophilic group and the amino group are stable in aqueous solution. While such bonds found in cationic lipids include amide bonds, ester bonds, ether bonds and carbamoyl bonds, preferred cationic lipids are those having a carbamoyl bond. An example of a preferred cationic lipid having a carbamoyl bond is DC-Chol. Those of skill in the art would readily understand that liposomes containing more than one cationic lipid species may be used to produce the complexes of the present invention. For example, liposomes comprising two cationic lipid species, lysyl-phosphatidylethanolamine and β-alanyl cholesterol ester have been disclosed (Brunette, E. et al. (1992) *Nucl. Acids Res.*, 20:1151).

It is to be further understood that in considering cationic liposomes suitable for use in mixing with drug and optionally with polycation, to form the complexes of this invention, the methods of the invention are not restricted only to the use of the lipids recited above but rather, any lipid composition may be used so long as a cationic liposome is produced.

Thus, in addition to cationic lipids, cationic liposomes used to form the complexes of the invention may contain other lipids in addition to the cationic lipids. These lipids include, but are not limited to, lyso lipids of which lyso-phosphatidylcholine (1-oleoyl lysophosphatidylcholine) is an example, cholesterol, or neutral phospholipids including dioleoyl phosphatidyl ethanolamine (DOPE) or dioleoyl phosphatidylcholine (DOPC) as well as various lipophylic surfactants, containing polyethylene glycol moieties, of which Tween-80 is one example. The lipid complexes of the invention may also contain negatively charged lipids as well as cationic lipids so long as the net charge of the complexes formed is positive and/or the surface of the complex is positively charged. Negatively charged lipids of the invention are those comprising at least one lipid species having a net negative charge at or near physiological pH or combinations of these. Suitable negatively charged lipid species include, but are not limited to, CHEMS (cholesteryl hemisuccinate), NGPE (N-glutaryl phosphatidlylethanolanine), phosphatidyl glycerol and phosphatidic acid or a similar phospholipid analog.

It is further contemplated that in the cationic liposomes utilized to form the complexes of the invention, the ratio of lipids may be varied to include a majority of cationic lipids in combination with cholesterol or with mixtures of lyso or neutral lipids. When the cationic lipid of choice is to be combined with another lipid, a preferred lipid is a neutral phospholipid, most preferably DOPE.

Methods for producing the liposomes to be used in the production of the lipidcomprising drug delivery complexes of the present invention are known to those of ordinary skill in the art. A review of methodologies of liposome preparation may be found in *Liposome Technology* (CFC Press New York 1984); *Liposomes* by Ostro (Marcel Dekker, 1987); *Methods Biochem Anal.* 33:337–462 (1988) and U.S. Pat. No. 5,283,185. Such methods include freeze-thaw extrusion and sonication. Both unilamellar liposomes (less than about 200 nm in average diameter) and multilamellar liposomes (greater than about 300 nm in average diameter) may be used as starting components to produce the complexes of this invention.

In the cationic liposomes utilized to produce the drug/lipid complexes of this invention, the cationic lipid is present in the liposome at from about 10 to about 100 mole % of total liposomal lipid, preferably from about 20 to about 80 mole % and most preferably about 20 to about 60 mole %. The neutral lipid, when included in the liposome, may be present at a concentration of from about 0 to about 90 mole % of the total liposomal lipid, preferably from about 20 to about 80 mole %, and most preferably from 40 to 80 mole %. The negatively charged lipid, when included in the liposome, may be present at a concentration ranging from about 0 mole % to about 49 mole % of the total liposomal lipid, preferably from about 0 mole % to about 40 mole %. In a preferred embodiment, the liposomes contain a cationic and a neutral lipid, most preferably DC-Chol and DOPE in ratios between about 2:8 to about 6:4. It is further understood that the complexes of the present invention may contain modified lipids, protein, polycations or receptor ligands which function as a targeting factor directing the complex to a particular tissue or cell type. Examples of targeting factors include, but are not limited to, asialoglycoprotein, insulin, low density lipoprotein (LDL), folate and monoclonal and polyclonal antibodies directed against cell surface molecules. Potential targets include, but are not limited to, liver, blood cells, endothelial cells and tumor cells. Furthermore, to enhance the circulatory half-life of the complexes, the positive surface charge can be sterically shielded by incorporating lipophilic surfactants which contain polyethylene glycol moieties.

It is to be further understood that the positive charge of the complexes of this invention may be affected not only by the lipid composition of the complex but also by the pH of the solution in which the drug/lipid complexes are formed. For example, increasing pH (more basic) will gradually neutralize the positive charge of the tertiary amine of the cationic lipid DC-Chol. In a preferred embodiment, the complexes of the present invention are produced, and stored, at a pH such that the complexes have a net positive charge and/or positively charged surface. A preferred pH range is pH 6.0–8.0, most preferably pH 7.0–7.8.

When a polycation is to be mixed with nucleic acid and cationic liposomes, the polycation may be selected from organic polycations having a molecular weight of between about 300 and about 200,000. These polycations also preferably have a valence of between about 3 and about 1000 at pH 7.0. The polycations may be natural or synthetic amino acids, peptides, proteins, polyamines, carbohydrates and any synthetic cationic polymers. Nonlimiting examples of polycations include polyarginine, polyornithine, protamines and polylysine, polybrene (hexadimethrine bromide), histone, cationic dendrimer, spermine, spermidine and synthetic polypeptides derived from SV40 large T antigen which has excess positive charges and represents a nuclear localization signal. In one embodiment, the polycation is poly-L-lysine (PLL).

In another more preferred embodiment, the polycation is a polycationic polypeptide having an amino acid composition in which arginine residues comprise at least 30% of the amino acid residues of the polypeptide and lysine residues comprise less than 5% of the amino acid residues of the polypeptide. In addition, preferably histidine, lysine and arginine together make up from about 45% to about 85% of the amino acid residues of the polypeptide and serine, threonine and glycine make up from about 10% to about 25% of the amino acid residues of the polypeptide. More preferably, arginine residues constitute from about 65% to about 75% of the amino acid residues of the polypeptide and lysine residues constitute from about 0 to about 3% of the amino acid residues of the polypeptide.

In addition to the above recited percentages of arginine and lysine residues, the polycationic polypeptides of the invention may also contain from about 20% to about 30% hydrophobic residues, more preferably, about 25% hydrophobic residues. The polycationic polypeptide to be used in producing drug/lipid/polycation complexes may be up to 500 amino acids in length, preferably about 20 to about 100 amino acids in length; more preferably, from about 25 to about 50 amino acids in length, and most preferably from about 25 to about 35 amino acids in length.

In one embodiment, the arginine residues present in the polycationic polypeptide are found in clusters of 3–8 contiguous arginine residues and more preferably in clusters of 4–6 contiguous arginine residues.

In another embodiment, the polycationic polypeptide is about 25 to about 35 amino acids in length and about 65 to about 70% of its residues are arginine residues and 0 to 3% of its residues are lysine residues.

The polycationic polypeptides to be used in formulating the complexes of the invention may be provided as naturally occurring proteins, particularly certain protamines having a high arginine to lysine ratio as discussed above, as a chemically synthesized polypeptide, as a recombinant polypeptide expressed from a nucleic acid sequence which encodes the polypeptide, or as a salt of any of the above polypeptides where such salts include, but are not limited to, phosphate, chloride and sulfate salts.

In one embodiment, a drug such as DNA could be complexed with an excess of polycationic polypeptide such that a net positively charged complex is produced. This complex, by nature of its positive charge, could favorably interact with negatively charged lipid (s) to form a DNA/lipid/polycationic polypeptide complex.

The transfection activity of a polycationic polypeptide/DNA/lipid complex of the invention in CHO cells, is preferably equal to or greater than the transfection activity of a poly-L-lysine/DNA/lipid complex in CHO cells when each polycation is complexed with the same cationic liposome and plasmid construct containing a reporter gene where reporter genes include, but are not limited to, the chloramphenicol acetyl transferase gene, the luciferase gene, the β-galactosidase gene and the human growth hormone gene, the alkaline phosphatase gene and a green fluorescent protein gene.

In producing nucleic acid/lipid/polycation complexes of the present invention, the ratio of polycation to nucleic acid is kept fixed while varying the amount of liposome. However, those of skill in the art would recognize that the ratio of polycation to nucleic acid will be affected by the charge density of the liposome to be mixed with the nucleic acid and polycation. For example, if the charge density of liposomes is decreased as a result of changes in the lipid composition of the liposome (eg decreasing the ratio of cationic lipid: neutral lipid in the liposome), the amount of polycation to be mixed with nucleic acid and liposome may be increased to compensate for the decrease in positive charge contributed by the liposomes. However, when polycation is utilized, it is preferred to use subsaturating amounts of polycation (i.e., amounts which will not saturate all the negative charge of the nucleic acid) in order to allow the cationic lipids to complex with the nucleic acid. Thus, in a preferred embodiment of the invention, a positive charge excess of lipid to nucleic acid is used even when polycation is mixed with lipid and nucleic acid. Amounts of polycation which may be mixed with 1 µg of nucleic acid and varying amounts of cationic liposomes in the present invention range from about 0.01 µg to about 100 µg of polycation per µg of nucleic acid, preferably from about 0.1 µg to about 10 µg of polycation per µg of nucleic acid.

Where purification of nucleic acid/lipid and nucleic acid/lipid/polycation complexes from excess free DNA, free liposomes and free polycation is desired, purification may be accomplished by centrifugation through a sucrose density gradient or other media which is suitable to form a density gradient. However, it is understood that other methods of purification such as chromatography, filtration, phase partition, precipitation or absorption may also be utilized. In a preferred method, purification via centrifugation through a sucrose density gradient is utilized. The sucrose gradient may range from about 0% sucrose to about 60% sucrose, preferably from about 5% sucrose to about 30% sucrose. The buffer in which the sucrose gradient is made can be any aqueous buffer suitable for storage of the fraction containing the complexes and preferably, a buffer suitable for administration of the complex to cells and tissues. A preferred buffer is pH 7.0–8.0 Hepes.

It is understood that in the present invention, preferred nucleic acid sequences are those capable of directing protein expression. Such sequences may be inserted by routine methodology into plasmid expression vectors known to those of skill in the art prior to mixing with cationic liposomes or liposomes and polycation to form the lipid-comprising drug delivery complexes of the present invention. The amount of nucleic acid mixed together with cationic liposomes or with cationic liposomes and polycation may range from about 0.01 μg to about 10 mg, preferably from about 0.1 μg to about 1.0 mg. It is understood that where the nucleic acid of interest is contained in plasmid expression vectors, the amount of nucleic acid recited above refers to the plasmid containing the nucleic acid of interest.

The purification of the nucleic acid/lipid and nucleic acid/lipid/polycation complexes of the present invention serves to concentrate the nucleic acids and lipids contained in the resultant complexes from about 50-fold to about 500-fold such that the lipid content contained in the complexes may be as high as about 40 μmol/ml and the nucleic acid content may be as high as about 2 mg/ml.

The nucleic acid/lipid/polycation complexes of the present invention produce particles of varying diameters upon formulation. As pointed out in the Background of Invention smaller particles tend to show greater size stability than larger particles. Furthermore, smaller particles may be more suitable for use as nucleic acid delivery vehicles. Particle diameters can be controlled by adjusting the nucleic acid/lipid/polycation ratio in the complex. FIG. 20 illustrates this fact for Lipid:Protamine Sulfate:DNA complexes. The diameter of the complexes produced by the methods of the present invention is less than about 400 nm, preferably less than about 200 nm, and more preferably less than 150 nm.

Figure 21:
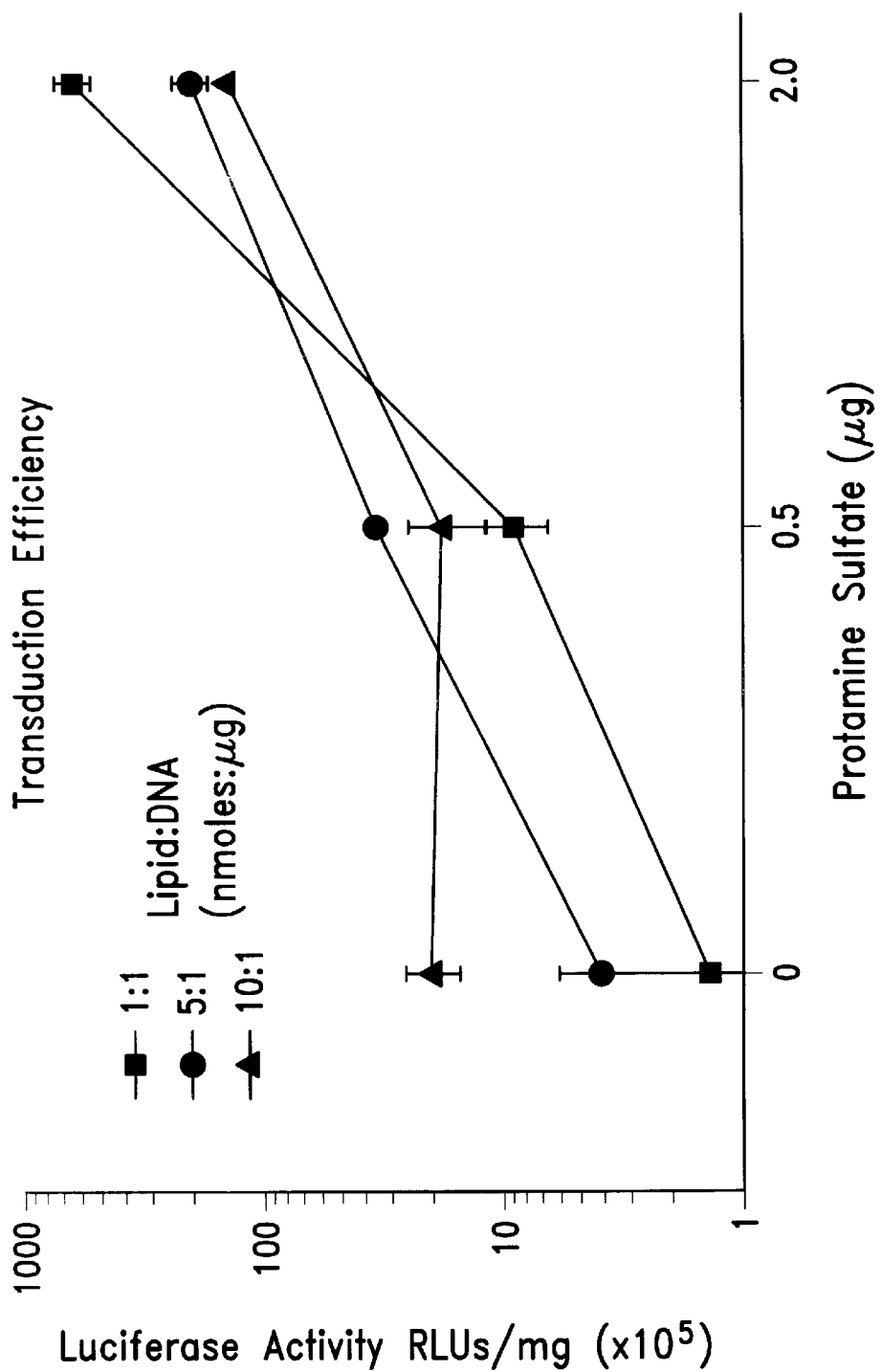
FIG. 21 shows the in vitro transfection activities of different LPD formulations in HeLa cells (a human cervical carcinoma cell line). The Protamine sulfate concentration of each formulation used is shown on the X axis. Transfection activity is indicated on the Y axis as relative light units of luciferase activity normalized to the amount of extracted protein.
Figure 22:
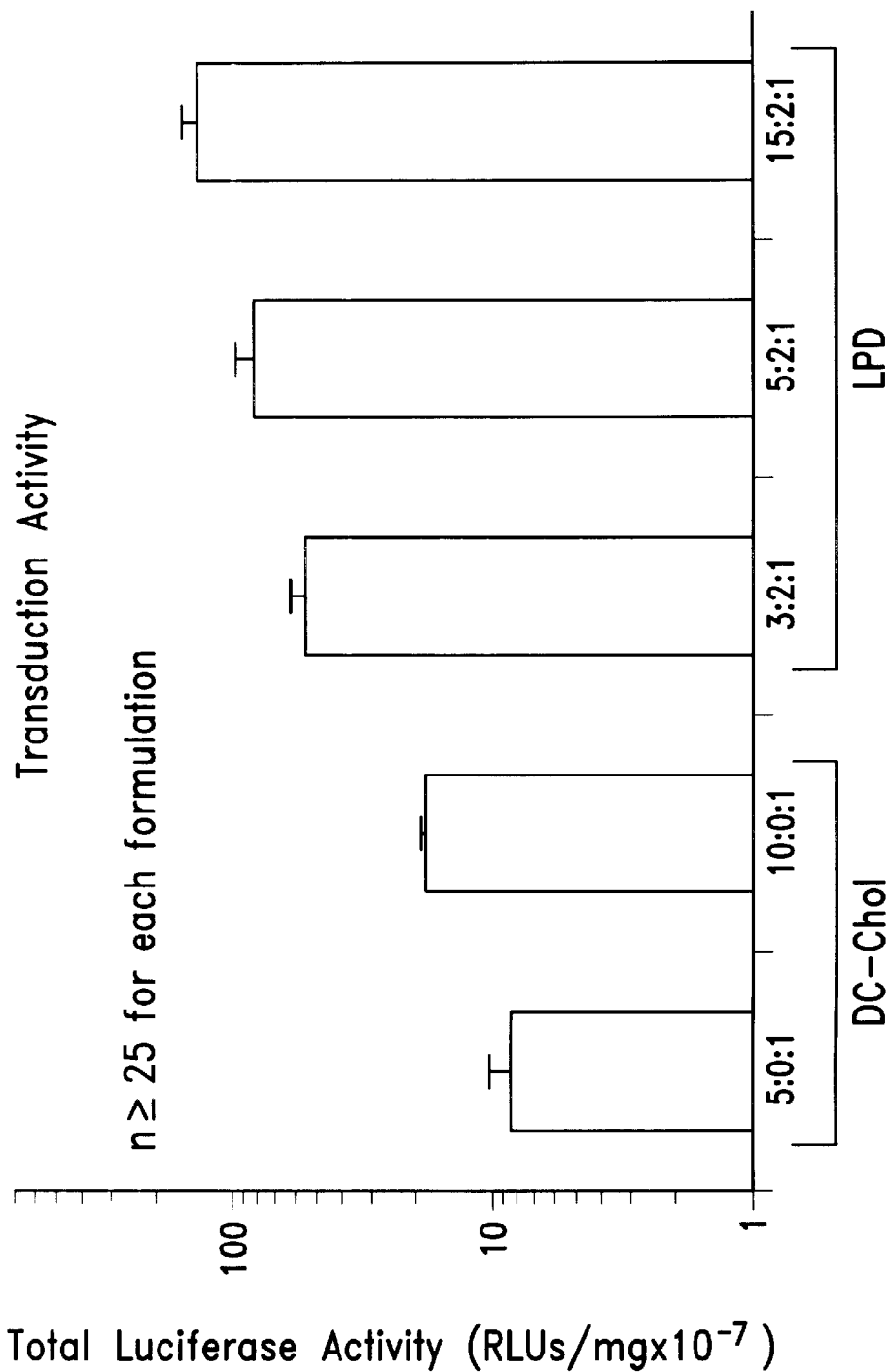
FIG. 22 shows the in vitro transfection activities of different LPD formulations in SKOV-3 cells (a human ovarian carcinoma cell line). The various DC-Chol and LPD delivery vehicles used in the study are indicated on the X axis. Transfection activity is indicated on the Y axis as relative light units of luciferase activity normalized to the amounts of extracted protein. The n value represents the number of individual experiments which were averaged for the data table. Each individual experiment consisted of replicates where n=3 or 6 for each formulation represented.
Figure 23:
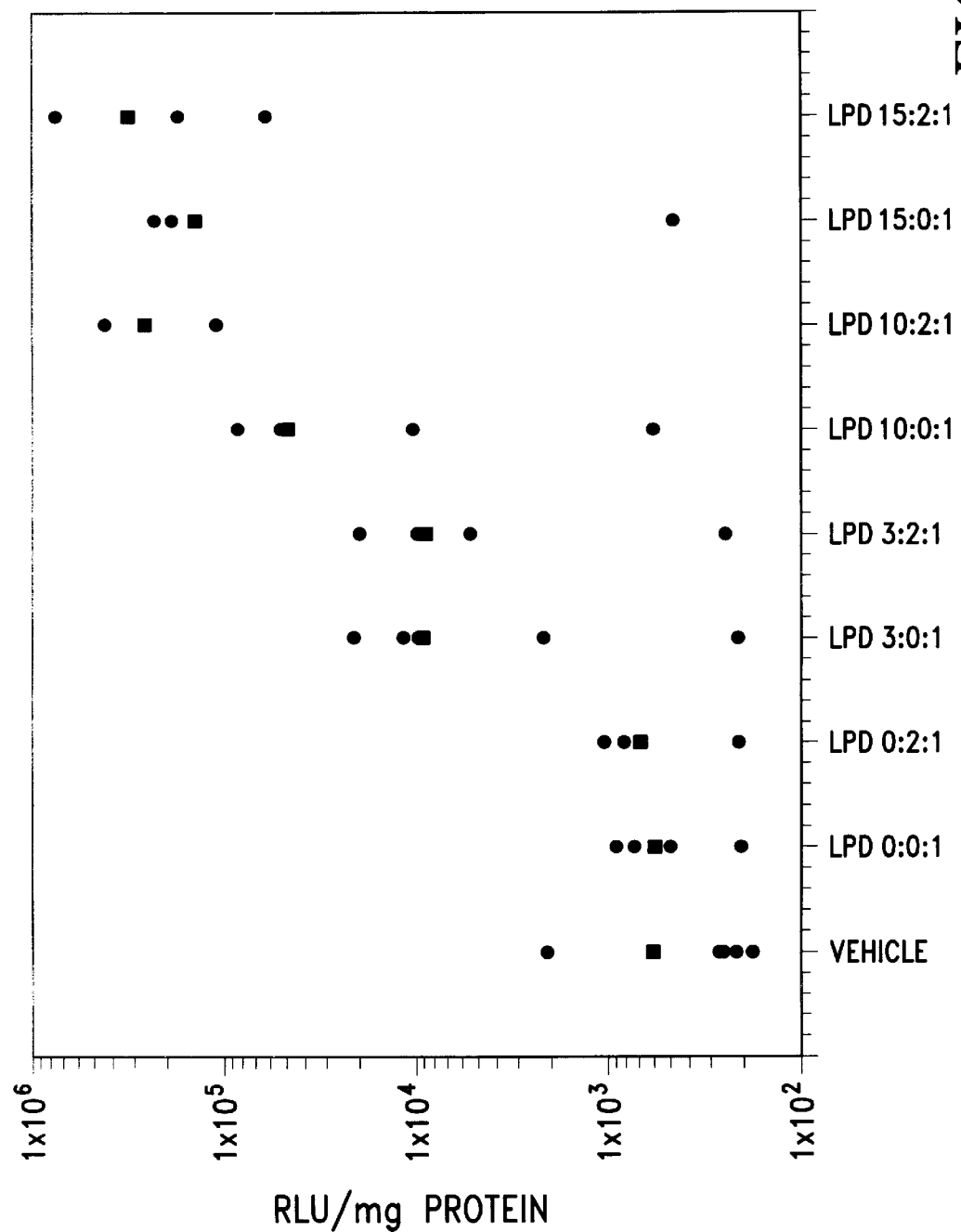
FIG. 23 shows the relationship between the Lipid:Protamine Sulfate:DNA formulation used in vivo to deliver pCMV-Luc intraperitoneally in an SKOV-3 murine model and the observed Luciferase expression activity. The composition of the delivery formulation is indicated on the X axis. The nomenclature used to describe the formulations follows the pattern of nanomoles of Lipid:μg Protamine Sulfate:μg DNA. Transfection activity is indicated on the Y axis as relative light units of luciferase activity. The graph shows the RLU/mg values obtained for each individual mouse (circles) and the average value per formulation (squares).

Nucleic acid/lipid/polycation ratios in the present invention further affect the biological activity of the complexes. The in vitro and in vivo transfection of mammalian cells can be facilitated by adjusting the relative amounts of nucleic acid, lipid and polycation. FIGS. 21, 22 and 23 present data demonstrating this effect for the Lipid/Protamine Sulfate/DNA mediated transfection of HeLa and SKOV-3 cells. Where the polycation is Protamine Sulfate and the nucleic acid is DNA, the nucleic acid/polycation ratio for the complex is between 1:0.01 and 1:100. The nucleic acid/polycation ratio is preferably between 1:0.1 and 1:10, more preferably between 1:0.5 and 1:5 and most preferably between 1:1 and 1:3.

The complexes formed by the methods of the present invention are stable for up to about one year when stored at 4° C. The complexes may be stored in 10% sucrose or a 5% dextrose solution upon collection from the sucrose gradient or they may be lyophilized and then reconstituted in an isotonic solution prior to use. In a preferred embodiment, the complexes are stored in solution. The stability of the complexes of the present invention is measured by specific assays to determine the physical stability and biological activity of the complexes over time in storage. The physical stability of the complexes is measured by determining the diameter and charge of the complexes by methods known to those of ordinary skill in the art, including for example, electron microscopy, gel filtration chromatography or by means of quasi-elastic light scattering using, for example, a Coulter N4SD particle size analyzer as described in the Examples. The physical stability of the complex is "substantially unchanged" over storage when the diameter of the stored complexes is not increased by more than 100%, preferably by not more than 50%, and most preferably by not more than 30%, over the diameter of the complexes as determined at the time the complexes were purified.

Assays utilized in determining the biological activity of the complexes vary depending on what drug is contained in the complexes. For example, if the drug is nucleic acid encoding a gene product, the biological activity can be determined by treating cells in vitro under transfection conditions utilized by those of ordinary skill in the art for the transfection of cells with admixtures of DNA and cationic liposomes. Cells which may be transfected by the complexes includes those cells which may be transfected by admixture DNA/liposome complexes. The activity of the stored complexes is then compared to the transfection activity of complexes prepared by admixture. If the drug is a protein, then activity may be determined by a bioassay suitable for that protein.

It is further understood by those of skill in the art that the complexes of the present invention may be used in vivo as vectors in gene therapy.

Therapeutic formulations using the complexes of the invention preferably comprise the complexes in a physiologically compatible buffer such as, for example, phosphate buffered saline, isotonic saline or low ionic strength buffer such as 10% sucrose in $H_2O$ (pH 7.4–7.6) or in Hepes (pH 7–8, a more preferred pH being 7.4–7.6). The complexes may be administered as aerosols or as liquid solutions for intratumoral, intravenous, intratracheal, intraperitoneal, and intramuscular administration.

Any articles or patent referenced herein are incorporated by reference. The following examples illustrate various aspects of the invention but are intended in no way to limit the scope thereof.

EXAMPLES

Materials

DOPE was purchased from Avanti Polar Lipid, Inc. (Alabaster, Ala.). pRSVL, a plasmid which encodes the luciferase gene under the control of Rous sarcoma virus long terminal repeat, (De Wet, J. R. et al. (1987) *Mol. Cell. Biol.*, 7:725–737) was amplified in *E. coli* and purified using the standard CsCl-EtBr ultracentrifugation method (Sambrook, J., Fritsch, E. F. and Maniatis, T., Molecular Cloning: A Laboratory Manual (2d ed) Cold Spring Harbor Laboratory Press: New York (1989)). All the tissue culture media were obtained from Gibco BRL (Gaithersburg, Md.). Human embryonic kidney 293 cells, CHO (Chinese Hamster Ovary cells), BL6 and BHK (Baby Hamster Kidney cells) cells were from American Type Culture Collection (Rockville, Md.). Mouse lung cells (MLC) are primary culture cells originally derived from the lung of a Balb/c mouse by Dr. S. Kennel (Oak Ridge National Laboratory, Tennessee). 293, BL6, BHK and MLC cells were cultured with DMEM media, CHO cells were cultured with F12 media, and C3 Hela cells were cultured in RPMI-1640 medium. All media was supplemented with 10% fetal bovine serum (Hyclone Laboratories, Inc., Logan, Utah.) and 100 unit/ml penicillin and 100 gg/ml streptomycin. Poly-L-lysine hydrobromide (MW 3000 and MW 25,600) and other chemicals were from Sigma (St Louis, Mo.).

DC-Chol was synthesized according to the method of Gao and Huang (1991) (Gao, X., and Huang, L. (1991) *Biochem. Biophys. Res. Commun.*, 179: 280–285) with modifications in the purification steps as follows: after the reaction, 10 ml hexane was added and the mixture was extracted three times with 10 ml water. The organic phase was collected and dried under vacuum at 4° C. The resulting solid was dissolved in a minimal amount of absolute ethanol with heat, and recrystallized in acetonitrile at 0° C. The purity of DC-Chol was at least >95%, as analyzed by TLC method and $^1$H-NMR and the yield of about 70% was a significant improvement over that of the previously reported method of Gao, X., and Huang, L. ((1 991) *Biochem. Biophys. Res. Commun.*, 179: 280–285).

METHODS

Preparation and Purification of Complexes

Cationic liposomes at a 20 mM total lipid concentration were prepared from DC-Chol and DOPE at various ratios by a sonication method, according to a published procedure (Gao, X., and Huang, L. (1991) *Biochem. Biophys. Res. Commun.*, 179: 280–285). Trace amount of $^3$H cholesteryl hexadecyl ether (Amersham, Arlington Heights, Ill.) was included for quantitation purpose. The size of these liposomes was between 100 to 150 nm in diameter, as determined by quasi-elastic light scattering using a Coulter N4SD particle sizer (Coulter Electronics, Inc., Hialeah, Fla.). Unless indicated otherwise in the following Examples, DNA/lipid complexes were prepared at a typical laboratory scale by adding amounts of free DC-Chol/DOPE liposomes as indicated in each Example in a volume of 1 ml of a 2 mM Hepes buffer (pH 7.6) to a 15×7.5 polystyrene culture tube (Baxter, McGraw Pare, Ill.), a micro-magnetic stirrer was placed in the tube, and the solution was well mixed. Amounts of pRSVL DNA as indicated in each Example were then added dropwise from a stock solution (0.2 mg/ml, in 2 mM Hepes buffer, pH 7.6) to the liposome solution over a period of 3 min. Trace amounts of pRSVL labeled with $^{32}$P using a nick translation kit (Promega, Madison, Wis.) and $^{32}$P dCTP (Amersham, Arlington Heights, Ill.) was included for the purpose of quantitation.

To prepare purified lipid/PLL/DNA complexes, an amount of the above 0.2 mg/ml DNA solution as indicated in each Example was added to 1 ml PLL/liposome mixture containing amounts of liposomes and PLL as indicated in each Example. DNA/lipid complexes were loaded on the top of a sucrose step gradient composed of 0.5 ml each of 5%, 7.5%, 10% and 15% sucrose (w/w) and DNA/lipid/PLL complexes were loaded on top of a sucrose step gradient composed of 0.5 ml each of 5%, 10%, 15%, 20%, 25% and 30% sucrose (w/w). The DNA/lipid and DNA/lipid/PLL complexes were then purified from free lipid and PLL by ultracentrifugation at 100,000 g for 30 min at 4° C. After centrifugation, fractions of 200 μl were taken from the top to the bottom of the tube. Aliquots from each fraction were assayed for both $^3$H and $^{32}$P radioactivity using a scintillation counter. Fractions that contained peak value of the $^{32}$P were collected and pooled. These pooled fractions were then assayed for particle size and for transfection activity.

In Vitro Transfection Assay

The biological activity of the above complexes were assayed by in vitro transfection of cells in the Examples as follows. Briefly, cells grown in 48 well plate were incubated with DNA/lipid complex diluted in 0.5 ml CHO-S-SFM (Gibco BRL) or with admixture DNA/liposome complex prepared according to Gao and Huang (1991) (Gao, X., and Huang, L. (1991) *Biochem. Biophys. Res. Commun.*, 179: 280–285). For transfection of pRSVL DNA using DC-Chol liposomes in the presence of PLL, liposomes were first mixed with PLL, then complexed with DNA. All transfections were performed for 4 hours at 37° C. After transfection, cells were further cultured for 36 hours in the appropriate media containing 10% fetal bovine serum. Cells were then washed with PBS and lysed with 100 μl of 1X lysis buffer provided by a luciferase assay kit (Promega, Madison, Wis.). A 4 μl sample of the lysate was assayed for luciferase activity using 100 μl substrate solution from the reconstituted luciferase assay kit and an AutoLumat LB953 luminometer (Berthold, Germany). Protein concentration from each lysate was assayed by a Coomassie blue dye method according to the manufacturer's protocol (Pierce, Rockford, Ill.).

Example 1

The Size Of The DNA/Lipid Complex Is Determined By The Ratio Of DNA To Lipid

This experiment was conducted to show that the size of the DNA-lipid complex formed by admixture changed as the ratio of DNA mixed with liposome varied. In brief, pRSVL plasmid DNA (2 μg) was mixed with varying amounts of DC-Chol/DOPE (3:2) liposomes in 2 mM Hepes buffer at pH 7.6 in a final volume of 500 μL and after 7 minutes, the size of the complex was determined with a Coulter N4SD laser light scattering particle sizer operating in the unimodel mode.

As shown in FIG. 1, large aggregates did not form when DNA was in excess (ratios of liposome to DNA less than 7) but at ratios of lipid to DNA that were charge neutral (~10), the size of the complex reached a maximum. In addition, when the ratio of liposome-to-DNA was kept constant at 10 nmoles/μg, the size of the complex increased as both DNA and liposome concentration increased and eventually formed precipitates. However, when the ratio of liposomes to DNA was increased, the size of the complex was progressively reduced until the size of the complex became constant (250–300 nm) when the ratio of liposome-to-DNA exceeded 25 nmoles lipid/μg DNA. This result may be due to the fact that the DNA was perhaps coated by excess liposomes and therefore aggregation between the complexes did not occur.

Based on the data presented in FIG. 1, lipid/DNA complexes were prepared using a liposome-to-DNA ratio of 50 nmoles/μg by slowly adding a DNA solution of 200 μg/ml to an excess amount (10 μmols) of liposome. The size of the complex formed was about 250 nm. When the ratio of liposome-to-DNA was changed to 25 nmoles/μg, the size of the complex increased to about 350 nm. The complexes formed using either the 25 nmole/μg or 50 nmole/μg ratios appeared to be physically stable since no precipitates formed during storage for four weeks at 4° C.

Example 2

Purification Of DNA/Lipid Complexes

Figure 2A:
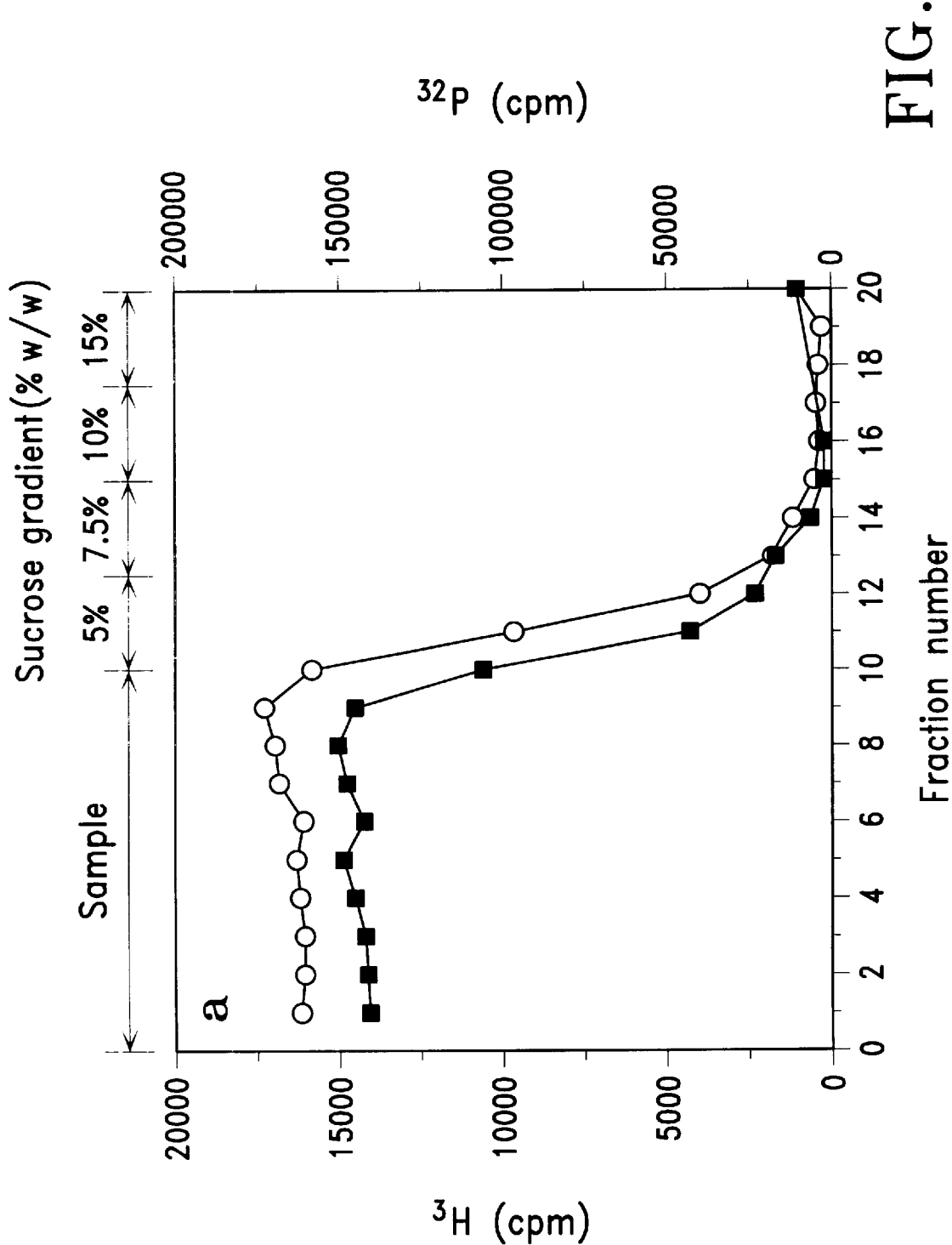
FIGS. 2A and 2B show the distribution of the liposome marker $^3$H-cholesteryl hexadecyl ether (○) and the $^{32}$P-DNA marker (■) among sucrose gradient fractions. The location of each fraction in the sucrose gradients of both
Figure 2B:
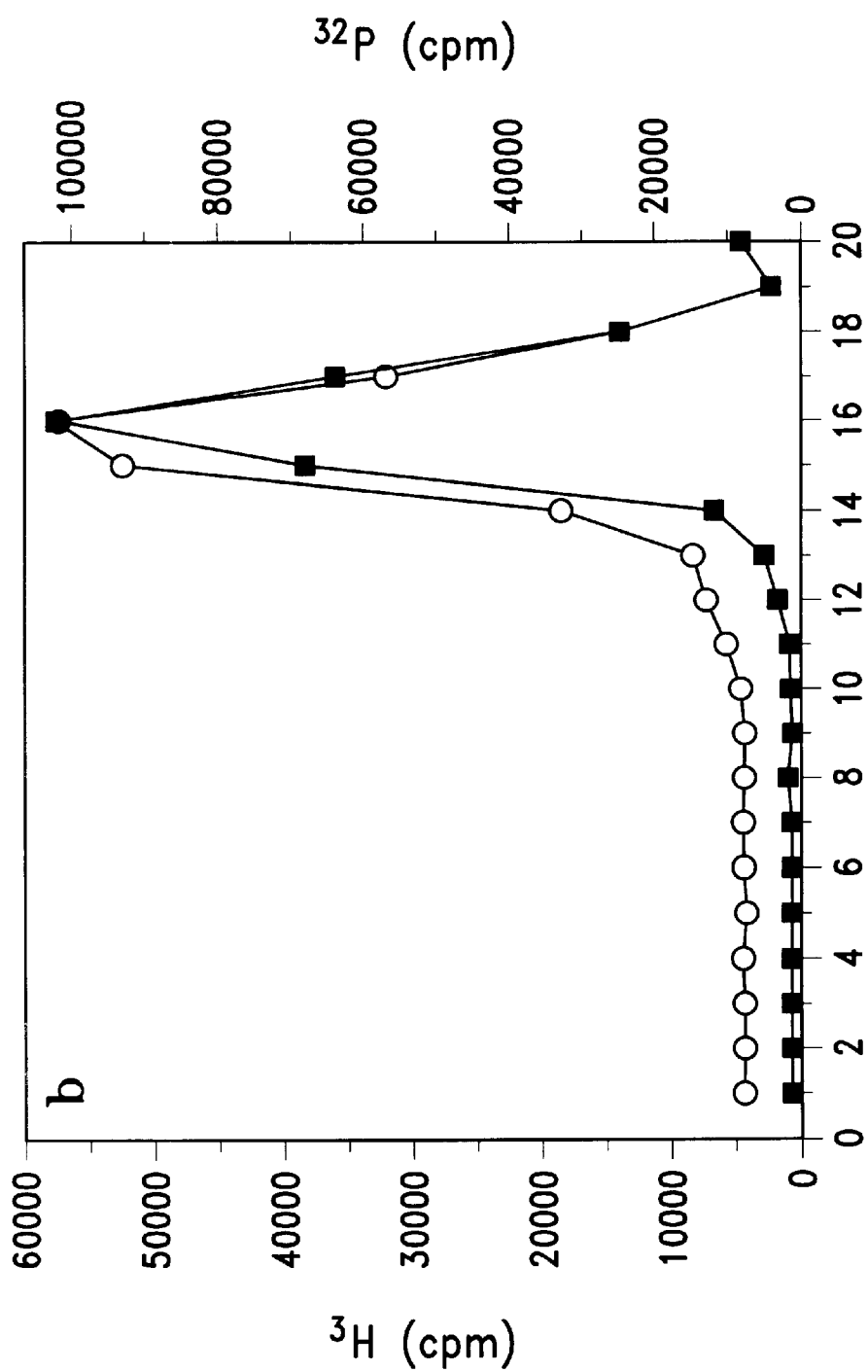

When DNA was mixed with liposomes at a ratio of 1 μg/50 nmoles, an excess of free liposomal lipids was observed to co-exist with the DNA/lipid complex. Since excess free lipids are toxic to cells, an experiment was conducted to determine if free liposomal lipids could be separated from the DNA/lipid complex by a density gradient ultracentrifugation method. In brief, free liposomes (10 μmoles of DC-Chol/DOPE (2:3) in a volume of 2 ml); free DNA (50 μg pRSVL in a volume of 2 ml) and DNA/lipid complex formed by mixing 20 μmoles DC-Chol/DOPE (2:3) and 0.4 mg pRSVL plasmid DNA (50 nmoles/μg) were each centrifuged for 30 minutes at 4° C. at 100,000 g over a gradient consisting of 0.5 ml each of 5%, 7.5%, 10% and 15% sucrose (W/W). Fractions of 200 μl were then collected from the top to the bottom of the tube and assayed for the distribution of DNA marker ($^{32}$P, ■) and lipid marker ($^3$H, O). FIGS. 2A and 2B show the results of typical separations of free liposomal lipid, free DNA (FIG. 2A) and DNA/lipid complex (FIG. 2B) on the sucrose gradient. The results presented in FIG. 2B show that after centrifugation, the complex formed a major band at the 10% sucrose layer. By comparison, FIG. 2A shows that most of the radioactivity of the free DNA or free liposomal lipids distributed at the top half of the tube and did not enter the sucrose gradient. In addition, although the peak of $^3$H and the peak of $^{32}$P in FIG. 2B co-existed at fraction number 16, there was a significant amount of the $^3$H distributed in fractions 1 to 10 indicating that the excess free liposomal lipids were well separated from the DNA/lipid complex.

Example 3
Physical Stability Of Purified Lipid/DNA And Lipid/PLL/DNA Complexes DNA/lipid complexes were formed by mixing 20 μmoles of liposomes of various DC-Chol/DOPE compositions (see Table 1) with 0.4 mg pRSVL plasmid DNA at a ratio of 1 μg DNA/50 nmoles lipid. Lipid/PLL/DNA complexes were formed by mixing 4 μmoles of liposomes of various DC-Chol/DOPE compositions with 1 mg PLL (MW=3000) and 0.4 mg pRSVL plasmid DNA. Both complexes were then purified from free lipids, free DNA and free PLL by sucrose gradient centrifugation as described in the Methods section. The peak fractions were collected and pooled. Pooled samples were then assayed for diameter immediately after collection (0 days) or after storage in 10% sucrose at 4° C. for 120 days. Table 1 shows the results of these assays.

TABLE 1

Physical stability of purified lipid/DNA and lipid/PLL/DNA pre-complexes

| Liposome composition (DC-chol/DOPE) | PLL (μg/μg DNA) | Size (nm) Day 0 | Size (nm) Day 120 | Purified complex Ratio of lipid/DNA (nmoles/μg) | Recovery of DNA (% Total) |
|---|---|---|---|---|---|
| 2:8 | 0 | 168 | 280 | 23.2 | 51 |
| 3:7 | 0 | 187 | 252 | 14.0 | 66 |
| 4:6 | 0 | 175 | 195 | 12.7 | 73 |
| 5:5 | 0 | 174 | 210 | 13.2 | 70 |
| 6:4 | 0 | 198 | 232 | 10.1 | 69 |
| 2:8 | 2.5 | 165 | 287 | 20.8 | 17 |
| 3:7 | 2.5 | 99 | 101 | 19.2 | 22 |
| 4:6 | 2.5 | 138 | 132 | 38.3 | 29 |
| 5:5 | 2.5 | 184 | 178 | 22.4 | 27 |

The data presented in Table 1 shows that purified lipid/DNA and lipid/PLL/DNA complexes were small (under 200 nm) in size at day 0 and that their size did not increase dramatically with storage. Further, the ratios of DNA-to-lipid in the purified complexes was between 10 to 23 nmoles lipid/gg DNA depending on the composition of the liposomes used and this ratio did not change after storage for 120 days. A reciprocal relationship between the concentration of DC-Chol in the liposomes and the amount of the lipid in the complex was also observed indicating that liposomes enriched with DC-Chol show stronger DNA binding or charge neutralizing activity than liposomes less enriched with DC-Chol. The far-right hand columns shows recovery of $^{32}$P-labeled DNA in the DNA/lipid and DNA/lipid/PLL complexes following their purification on the sucrose density gradient. The results show that recovery of DNA in the non-PLL containing complexes was higher than that observed for the PLL-containing complexes.

Example 4
Biological Activity Of The Purified Complexes In Various Cells Since the DNA/lipid complexes formed by a mixture of liposomes to DNA having a high lipid to DNA ratio were both small and stable over time, experiments were conducted to compare the transfection activity of these complexes to the activity of DNA/liposome complex prepared by the admixture method.

Figure 3:
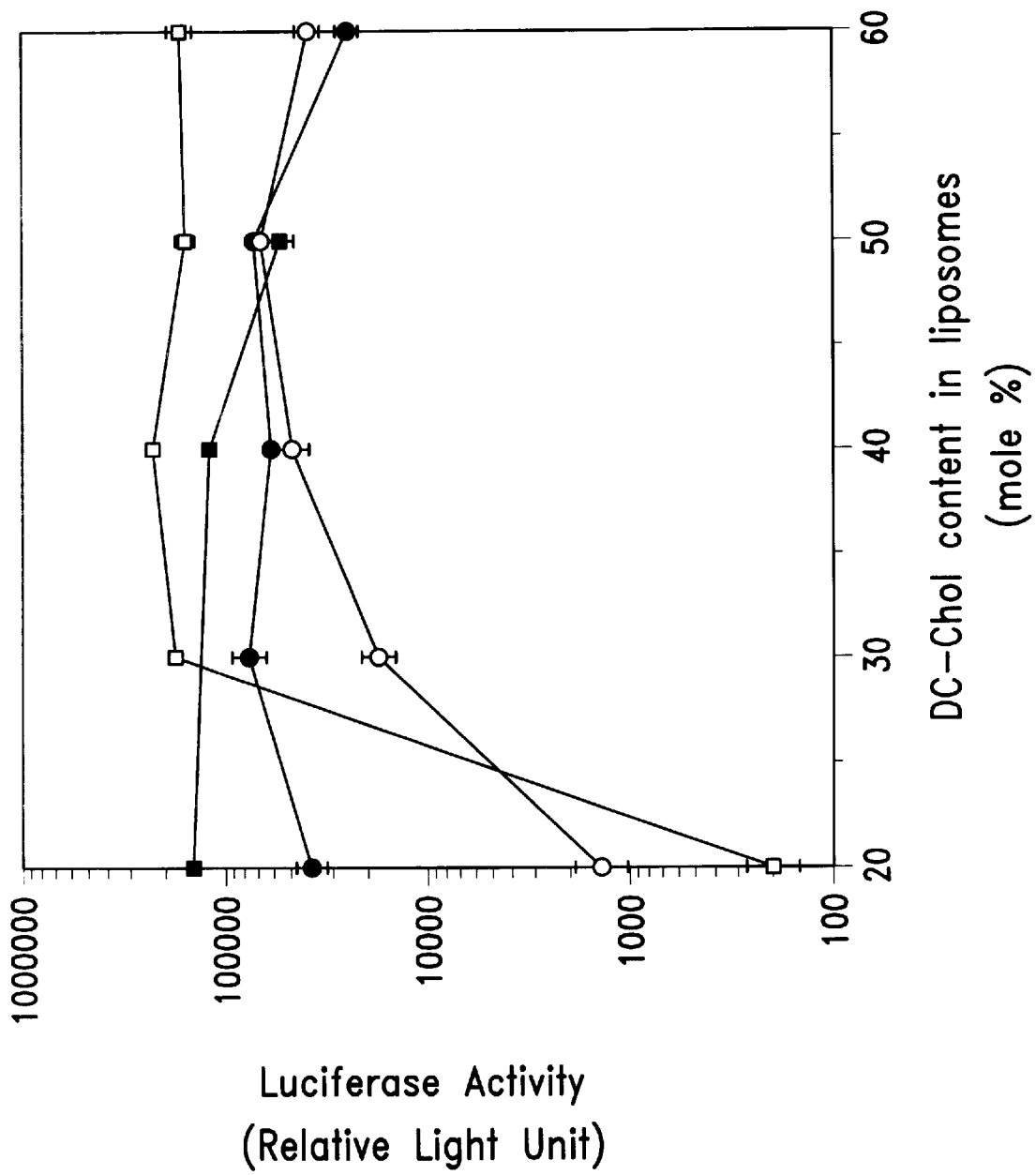
FIG. 3 shows the transfection activities in CHO cells of admixture DNA/liposome complex (○), admixture DNA/liposome/poly-L-lysine(PLL) complex (□) DNA/lipid complex (●) and DNA/lipid/PLL complex (■). The DC-Chol/DOPE liposomes used to form the above complexes contained varying mole % of DC-Chol as indicated at the bottom of FIG. 3. The DNA/lipid (●) and DNA/lipid/PLL (■) complexes were purified on a sucrose density gradient prior to being assayed for transfection activity. Transfection activity is indicated on the vertical axis as relative light units of luciferase activity.

In one experiment, CHO cells cultured in 48 well-plates were treated for 4 hours with an admixture of either 1 μg pRSVL and 10 nmoles DC-Chol/DOPE liposomes of different lipid compositions alone (○) or together with 1 μg PLL (MW=3,000) (□) or, the cells were treated with purified DNA/lipid complex (●) or purified DNA/lipid/PLL complex (■) formed by mixing 1 μg DNA with 50 nmoles DC-Chol/DOPE liposomes (DNA/lipid complex) or with 10 nmoles DC-Chol/DOPE liposomes and 1 μg PLL (DNA/lipid/PLL complex) followed by centrifugation through a sucrose density gradient as described in the Methods section. 36 hours after treatment, cells were lysed in 100 μl lysis buffer and 4 μl of the lysate was assayed for luciferase activity using 100 μl of luciferase substrate solution. Luciferase activity was then counted over a period of 20 seconds. The results presented in FIG. 3 show that the most preferred liposome composition for transfecting CHO cells was 40% DC-Chol and 60% DOPE. In addition, in the presence of additional 1 μg poly-L-lysine (PLL, MW=3,000), a 2–7 fold enhancement of the transfection activity was seen in most cases. Of particular interest, the activity of the purified DNA/lipid complex was similar to that of the admixture DNA/lipid complex when the same amount of DNA was added to cells. However, the transfection activity of the purified DNA/lipid/PLL complex was about 30% to 50% lower than that of the DNA/liposome/PLL complex prepared by the admixture procedure.

In order to determine that the results obtained in CHO cells were not cellspecific, the transfection activities of the purified DNA/lipid and DNA/lipid/PLL complexes in two other cells, BHK and mouse lung cells (MLC), were compared to that of DNA/liposome complexes formed by admixture.

In brief, cells (either BHK or MLC) grown in 48-well plates at 60% confluency were transfected with 1 μg pRSVL complexed with 10 nmoles of DC-Chol liposomes (admixture complex), with the same amount of DNA mixed with liposomes at a DNA/liposome ratio of 1 μg/50 nmols to produce purified DNA/lipid complex or with purified DNA/lipid/PLL complex prepared at a DNA/liposome/PLL ratio of 1 μg/10 nmols/2 μg. Cells were then harvested at 36 hours post-transfection, and the luciferase activity of the transfected cell lysates was determined as described in the Methods section. The results of these experiments are shown in Tables 2 and 3.

TABLE 2

Expression of luciferase gene in BHK cells transfected with pRSVL

| Liposome composition (DC-Chol/DOPE) | Luciferase Activity (Relative Light Units × 10$^{-3}$) | | |
|---|---|---|---|
| | Admixture DNA/liposome complex | Purified DNA/lipid complex | Purified DNA/lipid/PLL complex |
| 2:8 | 91.8 ± 9.5 | 110.1 ± 5.2 | 214.6 ± 41.1 |
| 3:7 | 61.2 ± 19.9 | 1886.8 ± 266.7 | 151.7 ± 62.9 |
| 4:6 | 438.2 ± 14.4 | 1638.8 ± 63.9 | 446.3 ± 16.9 |
| 5:5 | 837.8 ± 8 | 1015.0 ± 41.2 | 234.2 ± 46.4 |

TABLE 3

Expression of luciferase gene in mouse lung cells transfected with pRSVL

| Liposome composition (DC-Chol/DOPE) | Luciferase Activity (Relative Light Units x $10^{-3}$) | | |
|---|---|---|---|
| | Admixture DNA/liposome complex | Purified DNA/lipid complex | Purified DNA/lipid/PLL complex |
| 2:8 | 1.1 ± 0.7 | 0.4 ± 0.2 | 0.3 ± 0.1 |
| 3:7 | 1.5 ± 1.0 | 0.3 ± 0.0 | 4.1 ± 1.3 |
| 4:6 | 3.1 ± 0.2 | 2.0 ± 0.3 | 14.6 ± 3.1 |
| 5:5 | 0.1 ± 0.0 | 1.5 ± 1.2 | 10.1 ± 2.3 |

Interestingly, for the BHK cell line, the transfection activity of the purified DNA/lipid complex was significantly higher than that of the DNA/liposome complex formed by admixture. For cells such as MLC, which are difficult to transfect, purified complexes made from DNA/liposome/PLL mixtures were apparently superior to admixture complexes and to purified DNA/lipid complexes made without PLL.

In order to determine whether lipid/PLL/DNA complexes could be made using different ratios of lipid and nucleic acid and a different molecular weight PLL than that used in the previous examples, the following experiment was conducted. Lipid/poly-L-lysine/DNA complex was prepared from 20 µg pRSVL plasmid DNA, 10 µg poly-L-lysine (MW 25,600), and DC-chol/DOPE liposomes (4.5/5.5 molar ratio) at the ratios of lipid to DNA shown in Table 4. The resulting complexes were then purified by sucrose gradient ultracentrifugation as described in the methods section. An aliquot of the purified complex containing 0.5 µg of DNA was used to transfect CHO cells, and luciferase activity was then measured. The results of this experiment are shown below in Table 4.

TABLE 4

Effect of lipid/DNA ratio on purified complex containing poly-L-lysine (MW 25,600)

| Ratio (nmoles lipid/ µg DNA) | Composition of purified complex (nmoles lipid/ µg DNA) | Size of purified complex (nm) | Transfection activity[b] (counts (SD) x $10^{-3}$) |
|---|---|---|---|
| 3.3 | 1.1 | 89 | 108 (5) |
| 6.6 | 2.5 | 98 | 6,065 (604) |
| 12.5 | 4.3 | 101 | 5,846 (668) |
| 20.0 | 9.6 | 35 | 7,633 (977) |

The results show that in the presence of increased amounts of polycation, lower ratios of lipid to DNA may be used to produce DNA/lipid/polycation complexes having appreciable transfection activity.

Example 5
Transfection Activity of Stored Complexes

Figure 4:
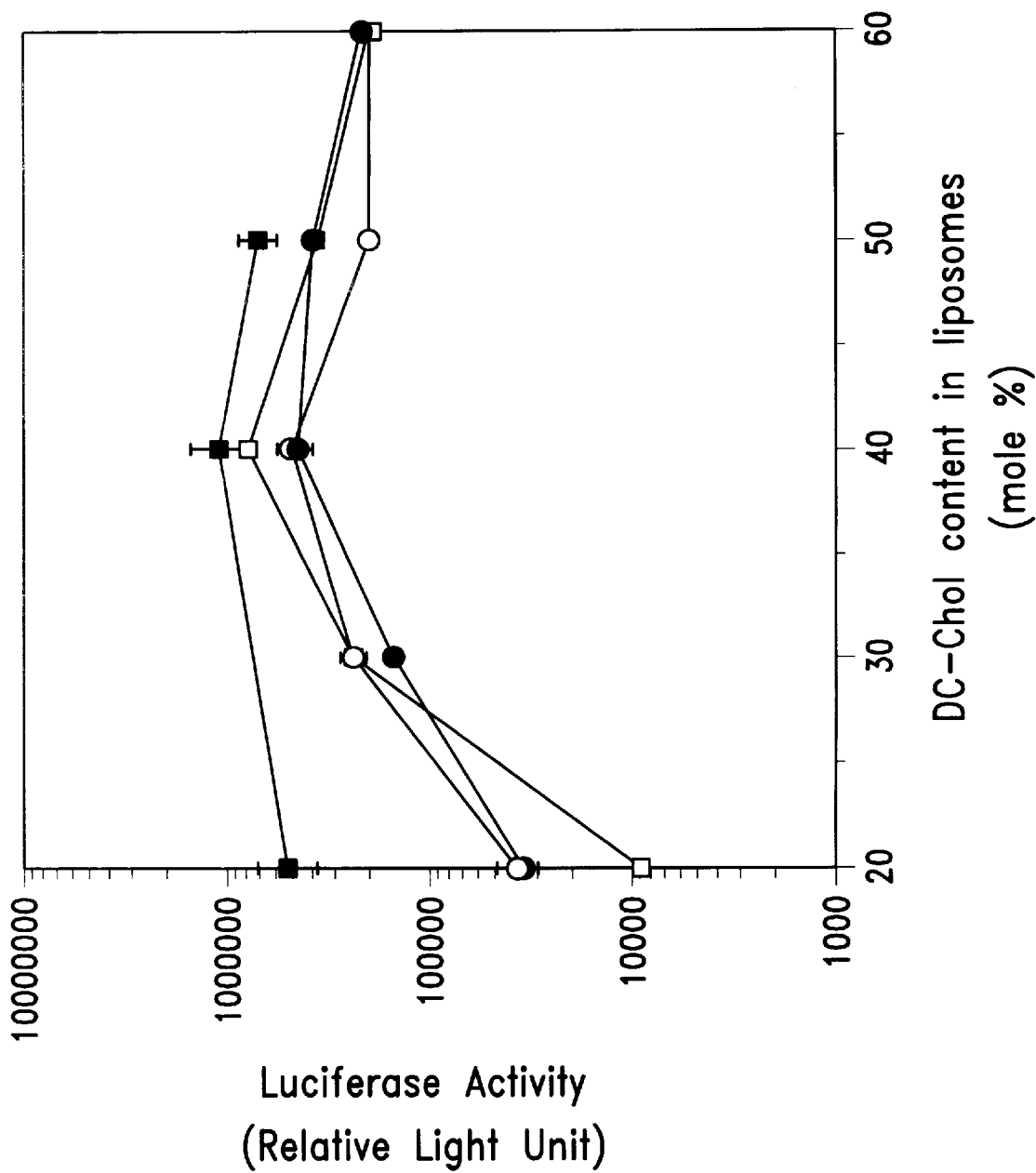
FIG. 4 shows the transfection activities of admixture DNA/liposome complex (○) and admixture DNA/liposome/PLL complex (□) compared to the transfection activities of DNA/lipid (●) and DNA/lipid/PLL complexes stored at 4° C. for 130 days following their purification on a sucrose density gradient. The DC-Chol/DOPE liposomes used to form the above complexes contained varying mole % of DC-Chol as indicated at the bottom of FIG. 4. Transfection activity is indicated on the vertical axis as relative light units of luciferase activity.

CHO cells cultured in 48 well-plates were treated for 4 hours with admixture of 1 µg pRSVL and 10 nmoles of DC-Chol/DOPE liposomes of different DC-Chol/DOPE compositions alone (○) or together with 1 µg PLL (mw= 3,000) (□), or with purified DNA/lipid (●) or DNA/lipid/PLL (■) complexes stored at 4° C. for 130 days in 10% sucrose. The purified complexes had been formed by mixing 1 µg pRSVL and 50 nmoles of DC-Chol/DOPE liposomes of different DC-Chol/DOPE compositions alone (DNA/lipid) or with 10 nmole of DC-Chol/DOPE liposomes and 1 µg PLL (DNA/lipid/PLL complex) followed by centrifugation through a sucrose density gradient as described in the Methods section. The results presented in FIG. 4 show that the luciferase activity of cell lysates prepared from cells transfected with the stored DNA/lipid and DNA/lipid/PLL complexes was comparable with the luciferase activity observed in cell lysates of cells transfected with the corresponding complexes prepared by admixture.

Example 6
Comparative Cytotoxicity Of DNA/Liposome Complexes Prepared By Admixture To That Of Purified DNA/Lipid Complexes Cell toxicity of the different complexes was studied in CHO cells as follows. CHO cells were treated with admixture DNA/liposome complex (○), admixture/liposome/PLL complex (□); purified DNA/lipid complex (●); or purified DNA/lipid/PLL complex (■). The admixture complexes were formed by mixing 1 µg pRSVL DNA with 10 nmoles DC-Chol/DOPE liposomes of different DC-Chol/DOPE compositions alone or together with 1 µg PLL (mw=3,000). The purified complexes were formed by mixing 1 µg pRSVL DNA with 50 nmoles DC-Chol/DOPE liposomes alone (DNA/lipid complex) or with 10 nmoles DC-Chol/DOPE liposomes and 1 µg PLL (DNA/lipid/PLL complex) followed by centrifugation through a sucrose density gradient as described in the Methods section. 36 hours after treatment, the cells were lysed, protein was extracted and then quantitated by a Coomassie blue dye method.

Figure 5:
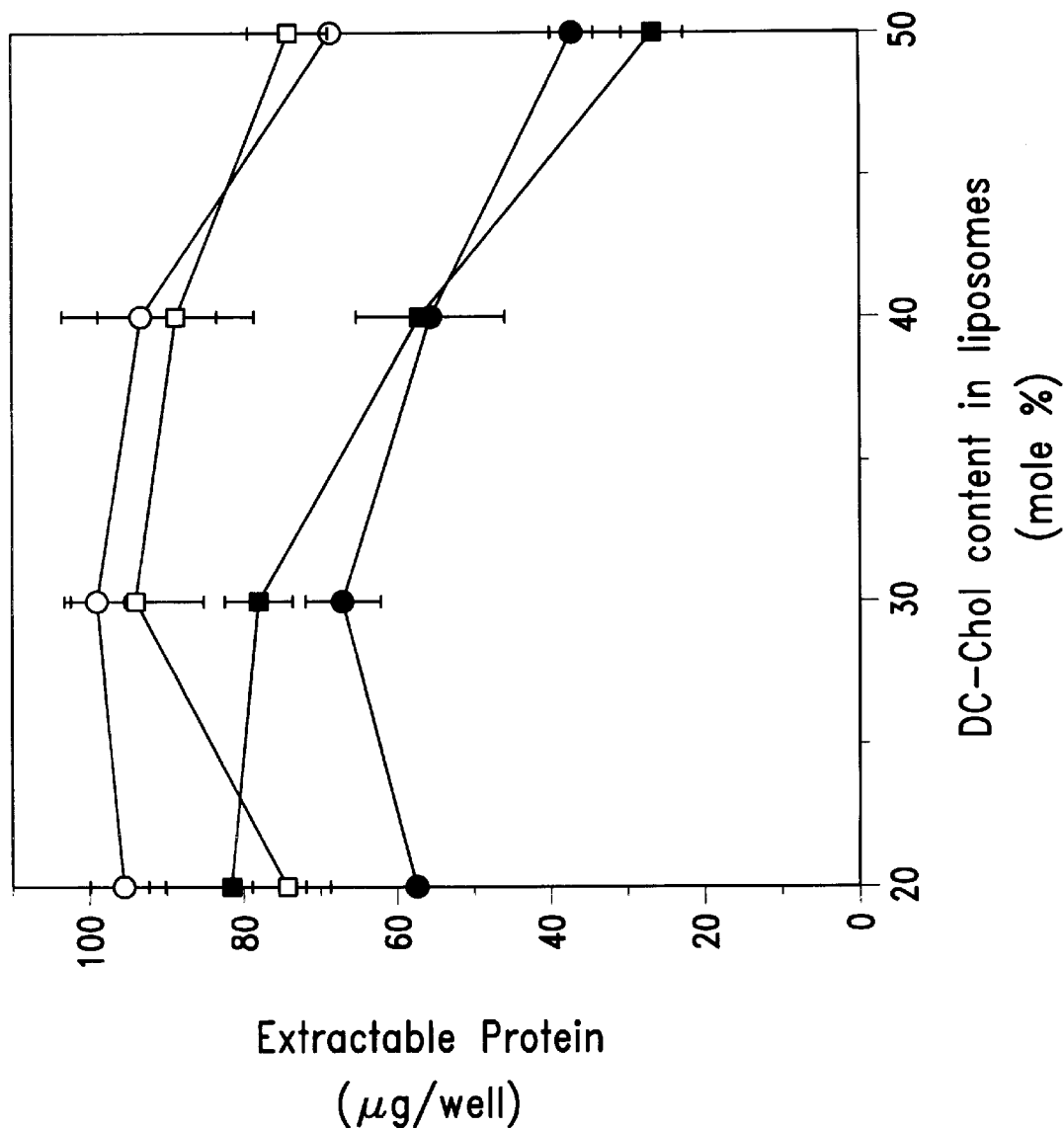
FIG. 5 shows the concentration of extractable protein from CHO cells, 36 hours after the cells were treated with admixture DNA/liposome complex (○); admixture DNA/liposome/PLL complex (□); DNA/lipid complex (●); or DNA/lipid/PLL complex (■). The DNA/lipid and DNA/lipid/PLL complexes were purified on a sucrose density gradient prior to being assayed for transfection activity. The DC-Chol/DOPE liposomes used to form the above complexes contained varying mole % of DC-Chol as indicated at the bottom of FIG. 5.
Figure 6:
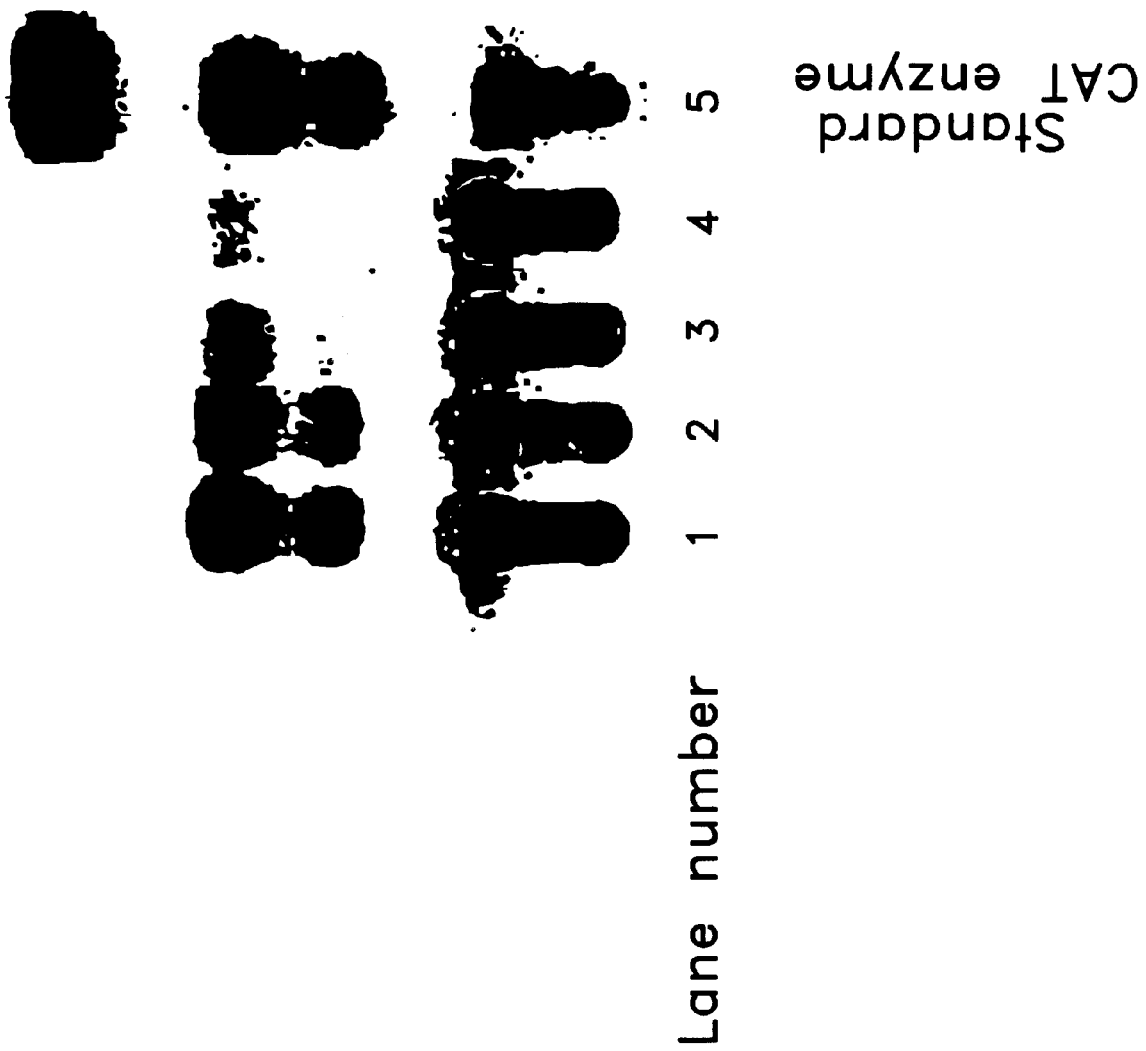
FIG. 6 shows the results of CAT assays of tumor extracts prepared from mice having ovarian tumors. 2×10$^6$ human ovarian carcinoma cells were subcutaneously injected into SCID mice at day 0. On day 14, 100 $\mu$l solutions containing pUCCMVCAT DNA (contains the chloramphenicol acetyl transferase gene of *E. coli*) 30 μg) complexed with DC-Chol liposomes (30 nmoles) in the form of admixture (lanes 1 and 2; duplicate samples) or the same amount of DNA in the form of purified complex (prepared from DNA:DC-chol liposome at ratio 1 μg/25 nmoles, lanes 3 and 4; duplicate samples) were directly injected into tumors. 48 hours following transfection, the mice were sacrificed and tumor extract containing 100 μg protein was assayed for CAT activity. Lane 5 shows positive control CAT activity for standard *E. coli* CAT.

FIG. 5 shows the results of this experiment where the amount of total extractable protein recovered at the end of the experiment serves as an indicator of the portion of the cells which survived after the indicated treatment. The data presented shows that while the purified complex appeared to be slightly more toxic to the cells than the admixture DNA/liposome complex, morphologically, the transfection did not cause any serious cytotoxic effects in cells treated with either admixture complexes or the purified complexes, except that the cells treated with purified complexes containing high mole % DC-Chol were less confluent at the end of the experiment.

Example 7
In Vivo Transfection of Tumors By Purified DNA/Lipid Complexes $3 \times 10^6$ human ovarian carcinoma cells were injected subcutaneously into SCID mice at day 0. 14 days later, 100 µl solutions containing pUCCMVCAT DNA (30 µg) complexed with DC-Chol (3:2 DC-Chol:DOPE) liposomes (30 nmoles) in the form of admixture (lanes 1 and 2) or the same amount of DNA in the form of purified DNA/lipid complex (prepared from DNA and DC-Chol liposomes at ratios of 1 µg DNA/25 nmoles lipid) were directly injected into tumors. Animals were sacrificed 2 days later and tumor extracts containing 100 µg protein were assayed for CAT activity at 37° C. according to Ausubel, et al. (1991) Current Protocols in Molecular Biology (Wiley, Boston), Vol. 1, pp. 9.6.2–9.6.5). The results show that purified complex, while prepared under non-optimal conditions, exhibited in vivo transfection activity.

Example 8
Comparative Transfection Activity of Purified and Unpurified DNA/Lipid/PLL Complexes With Admixture DNA/Lipid Complex The transfection activities of purified and unpurified DNA/Lipid/PLL complexes and admixture DNA/lipid complex in three cell lines (293, BL6 and C3) were measured as follows:

Purified DNA/lipid/PLL complex was formed by mixing 1 μg pRSVL DNA with 10 nmoles DC-Chol/DOPE liposomes (2:3 mol/mol) and 1 μg PLL (MW=25,600) followed by purification via centrifugation through a sucrose density gradient as described in the Methods section.

Unpurified DNA/lipid/PLL complexes were formed by mixing 100 μg pRSVL DNA with 80 μg PLL (MW=25,600) and 1702 nmol DC-Chol/DOPE (2:3 mol/mol) liposomes (i.e. a DNA/lipid/PLK ratio of 1 μg DNA/17 nmol lipid/0.8 μg PLL) in a final volume of 500 μl of water. 20 μl of the unpurified DNA/lipid/PLL complex (i.e. 4 μg DNA, 3.2 μg PLL and 68.1 nmol lipid) was then added to 780 μl of serum free medium appropriate for the cell line to be transfected.

Admixture DNA/lipid complex was formed by mixing 1 μg pRSVL DNA with 10 nmols of DC-Chol/DOPE (3:2 mol/mol) liposomes.

293, C3 and BL6 cells grown to 80% confluence in 24-well plates were transfected for four hours at 37° C. with 1 μg of DNA in the form of purified DNA/lipid/PLL complex, admixture DNA/lipid complex or unpurified DNA/lipid/PLL complex. After transfection, cells were further cultured for 36–48 hours in the appropriate media containing 10% fetal calf serum. Luciferase activity was then measured as described in the Methods section.

Figure 7A:
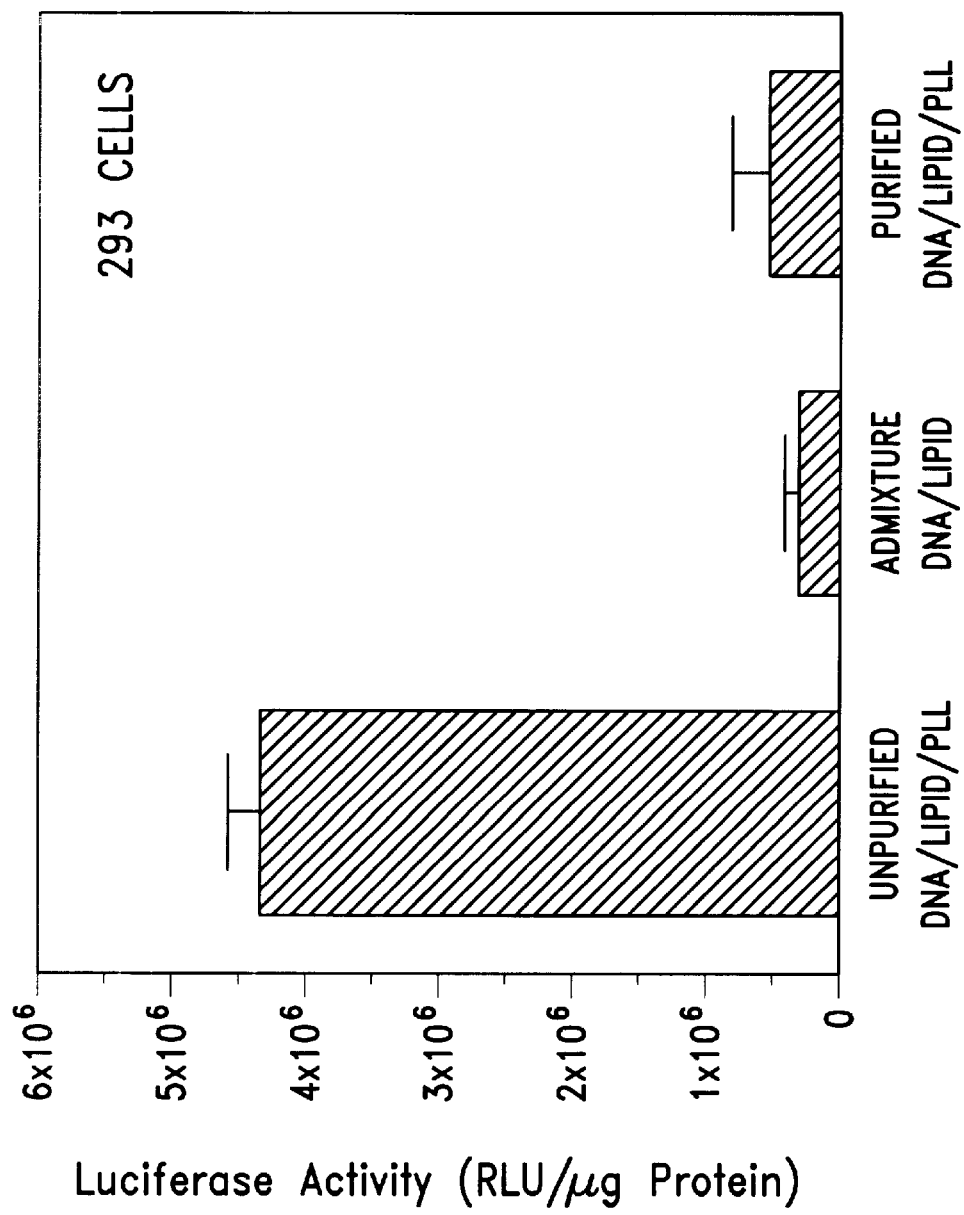
FIGS. 7A–7C show the transfection activities of admixture DNA/lipid complex and purified and unpurified DNA/lipid/PLL complexes in 293 cells (FIG. 7A) C3 cells (FIG. 7B) and BL6 cells (FIG. 7C). Transfection activity is indicated on the vertical axis of FIGS. 7A–7C as relative light units of luciferase activity.
Figure 7B:
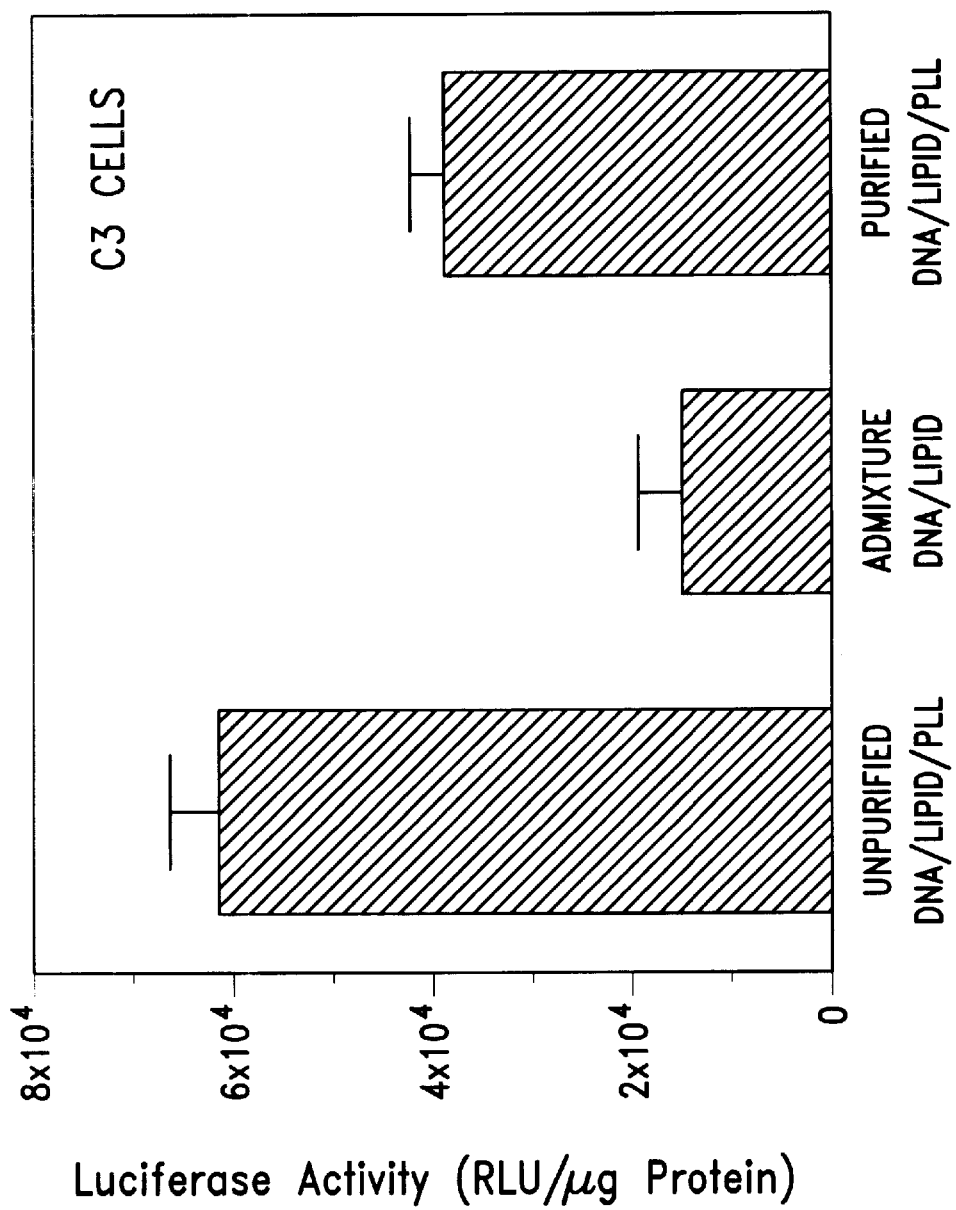
Figure 7C:
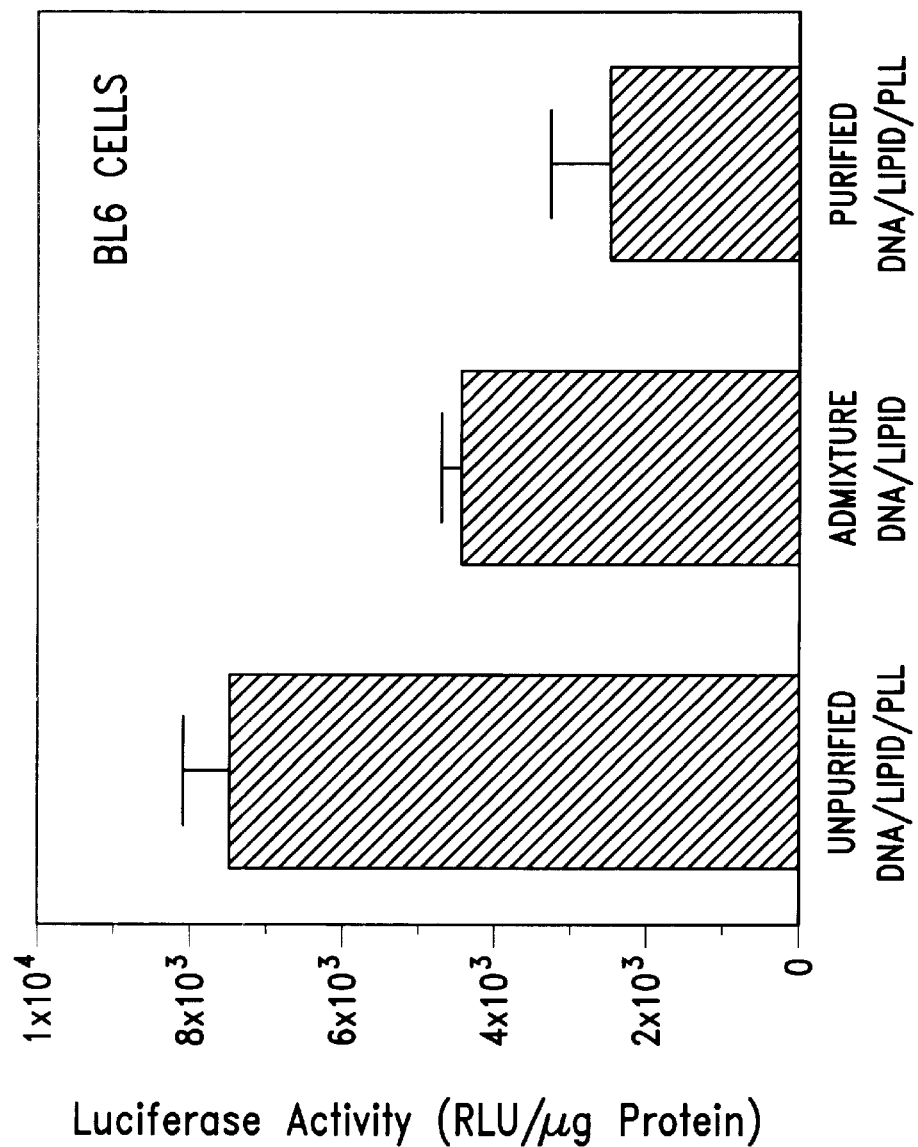

The results presented in FIGS. 7A (293 cells) 7B (C3 cells) and 7C (BL6 cells) demonstrate that the unpurified DNA/lipid/PLL complex exhibited the highest transfection activity in all three cell lines tested.

Materials and Methods for Examples 9–14 and in FIGS. 8–19

Plasmid DNA

The plasmid DNA used for all experiments consisted of a luciferase (LUC) reporter gene driven by the human cytomegalovirus (CMV) immediate early promoter and cloned into a pUK21 backbone. Plasmid DNA was prepared by growing bacterial stocks in a glycerol enriched Terrific Broth (TB) media. The bacteria was subject to detergent and alkaline lysis, propanol precipitation and treatment by high salt to remove high molecular weight RNA. The resulting supernatant was subjected to size exclusion chromatography to separate low molecular RNA from plasmid DNA. The DNA was shown to be absent of chromosomal DNA or RNA by gel electrophoresis and had an $A_{260/280}$ ratio between 1.80–1.90 as determined spectrophotometrically.

Linosomes

DC-Chol was synthesized as previously described (Gao and Huang, (1991) *Biochem. Biophys. Res. Commun.*, 179:280–285)). DOPE was purchased from Avanti Polar Lipids, Inc. DC-Chol liposomes were produced by microfluidization at a 6:4 molar ratio (DC-Chol to DOPE) and to a concentration of 2 μmol/ml (1.2 mg/ml of total lipid) as previously described in Int. J. Pharm. 14:34:30 1996.

Polycations

Poly-L-Lysine (MW 18,000–19,200), Protamine Free Base (Grade IV), Protamine Phosphate (Grade X), Protamine Chloride (Grade V), Protamine Sulfate (Grade II), Protamine Sulfate (Grade III), and Protamine Sulfate (Grade X) were all obtained from Sigma Chemical Co. Protamine Sulfate, USP was obtained from Elkins-Sinn, Fujisawa or from Eli Lilly and Company. All of the protamines were from salmon sperm except the grade III which was from herring.

Transfection of Mammalian Cells In Vitro

CHO cells were seeded into a 48-well plate and grown in F-12 media supplemented with 10% Fetal Bovine Serum (FBS) in a 37° C. incubator in a 5% $CO_2$ atmosphere. The cells were exposed to DNA complexed to DC-Chol liposomes with or without a polycation such as protamine or poly-lysine and allowed to transfect for 5.5–6 hours after which the transfection media (Hanks buffer) was replaced with fresh F-12 media supplemented with 10% Fetal Bovine Serum (FBS). Typically, 8 μg of Protamine (or 4 μg of poly-lysine) were mixed with 4 μg of DNA in a 1 ml volume of Hanks buffer in a 4 ml tube for approximately 5–15 run at room temperature. A second 4 ml tube containing 30 nmol of DC-Chol liposomes in 1 ml of Hanks buffer was added to the 1 ml sample of DNA/polycation and allowed to complex for 5–15 minutes at room temperature. After mixing, 0.5 ml aliquots (containing 1 μg DNA, 2 μg protamine or 1 μg poly-l-lysine, and 7.5 nmol of DC-Chol liposomes) were added to each well of the 48-well plate. The cells were allowed to incubate for a total of 35.5–38.5 hrs prior to being assayed for luciferase activity. Each point shown in FIGS. 8 and 9 represents the mean (with standard deviation) luciferase activity of three to four data points and are normalized to protein context.

In vitro transfection assays for HeLa cells (available from ATCC) and the SKOV-3 human ovarian carcinoma cell line (available from ATCC) were run under the same conditions as described above for CHO cells.

Luciferase Assay

CHO cells were allowed to transfect for 4–8 hours in transfection media and then allowed to incubate in F12+10% FBS for an additional 32–44 hours. The media was then aspirated and the cells were washed once with a 0.9% sodium chloride solution. The cells were lysed with 100 μl of lysis buffer (2 mM EDTA, 100 mM Tris, 0.05% Triton X-100) per well and subjected to one cycle of freeze-thaw. The cell lysates were collected, briefly centrifuged to pellet the cellular debris, and 10 μl was used for the luciferase assay. The samples were loaded into an AutoLumat LB953 (Berthold) Luminometer, 100 μl of the luciferase substrate (Promega) was added to the cell lysate, and the relative light units (RLU) of each sample were counted for 20 seconds. Samples were also assayed by Coomassie Blue Plus Protein Reagent (Pierce) and normalized to the protein content in each sample.

Example 9

Comparison of the Ability of Protamine Sulfate USP (Elkins-Sinn) and Poly-L-Lysine to Increase Transfection Activity in CHO Cells Protamines are naturally occurring cationic proteins which are characterized as being small (mw=4,000), extremely basic, and containing a large amount of arginine (Ando et al., (1973) in Protamines—Isolation, Characterization, Structure and Function (Springer-Verlay, New York) pp. 3–87)). Protamines are only found in the head of mature sperm and their sole function is to condense DNA such that it can be efficiently packaged and ultimately expressed within the nucleus of an egg. Protamines are typically purified from fish (salmon or herring) sperm. These proteins are approximately 30–35 amino acids in length and about two thirds (2/3) of these residues are arginine. The arginine residues are found in clusters of 4–6 in four distinct regions. About one fourth of the remaining residues are hydrophobic, resulting in evenly spaced hydrophobic and hydrophilic regions. The result of this unique arrangement of amino acids is that the protamine molecule is forced to assume an α-helical structure in the presence of nucleic acids. The spacing of the amino acids in protamine parallels the spacing of the bases in DNA. As a result, the protamine α-helical structure aligns along the major groove of DNA and associates strongly with the DNA without changing its conformational state. It can also cross-link with adjacent DNA strands producing a highly ordered, condensed DNA/protamine complex (Warrant and Kim, (1978) supra). While poly-lysine and poly-arginine have also been shown to condense DNA, they lack the fine structural characteristics found in protamine. As a result, the condensation by poly-lysine or poly-arginine results in a complex which is structurally different. This results in a change in the conformational and crystalline state of DNA from the biologically active B-form (as found in protamine) to an inactive crystalline A-form (Subirana, (1983) in the Sperm Cell ed. Andre, J. (Martainui, Nizeroff, the Hague), pp. 197–213)).

Accordingly, an experiment was conducted in which increasing amounts of salmon sperm protamine sulfate, USP or poly-L-Lysine were added to 1 µg of DNA and allowed to associate prior to the addition of 7.5 nmol of DC-Chol liposomes.

Figure 8A:
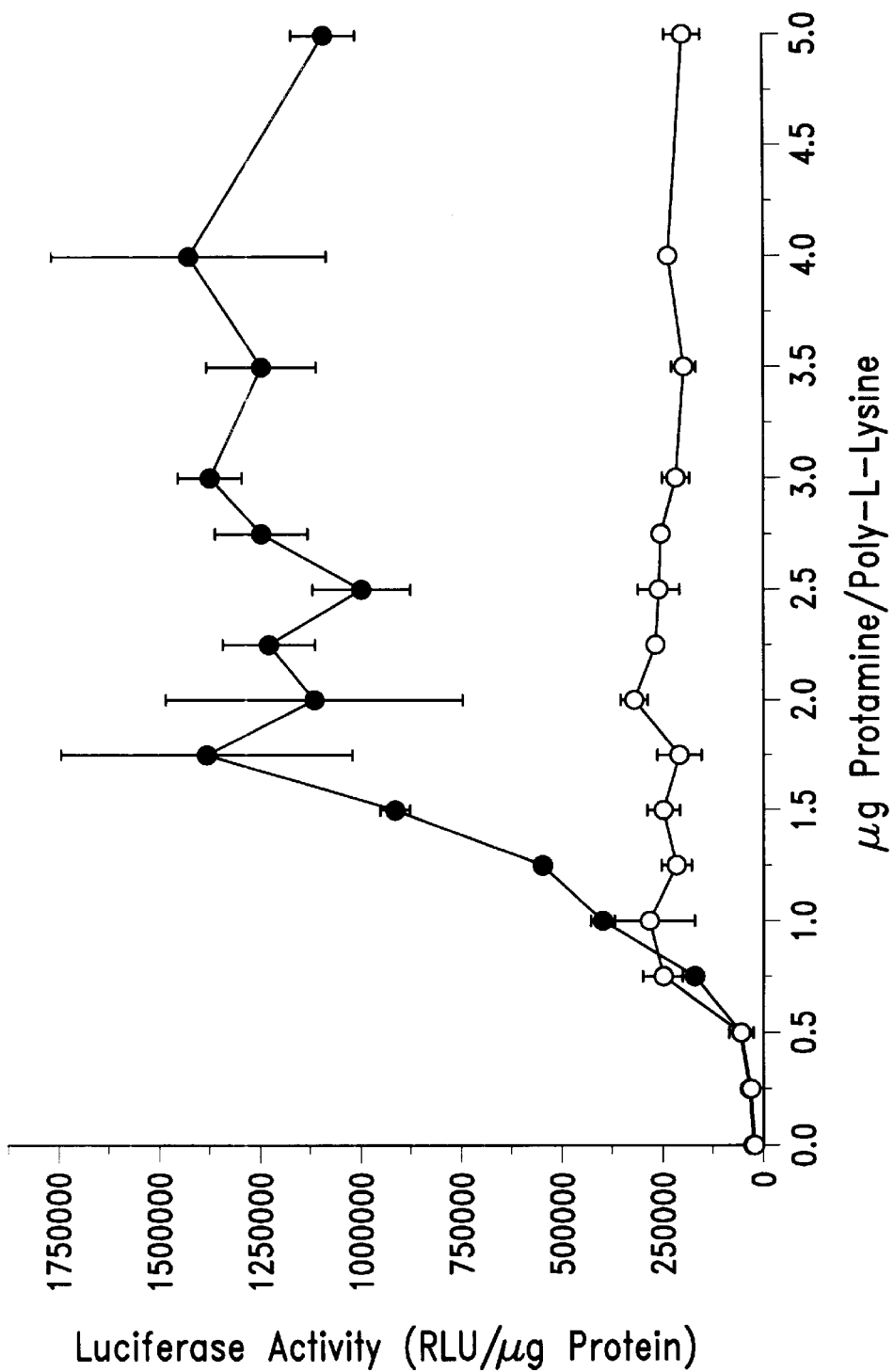
FIGS. 8A and 8B show a comparison of the ability of protamine sulfate, USP (PS) and poly-L-Lysine (PLL) to increase the transfection activity in CHO and 293 cells, respectively. Varying amounts of PS (●) or PLL (○) were added to 1 μg of pUK-21 CMV LUC DNA prior to complexation, with 7.5 nmol of DC-Chol liposomes per well. Transfection, luciferase, and protein assays were performed as described in Example 9 and each data point represents the mean (with standard variation) of three data points and are normalized to protein content.
Figure 8B:
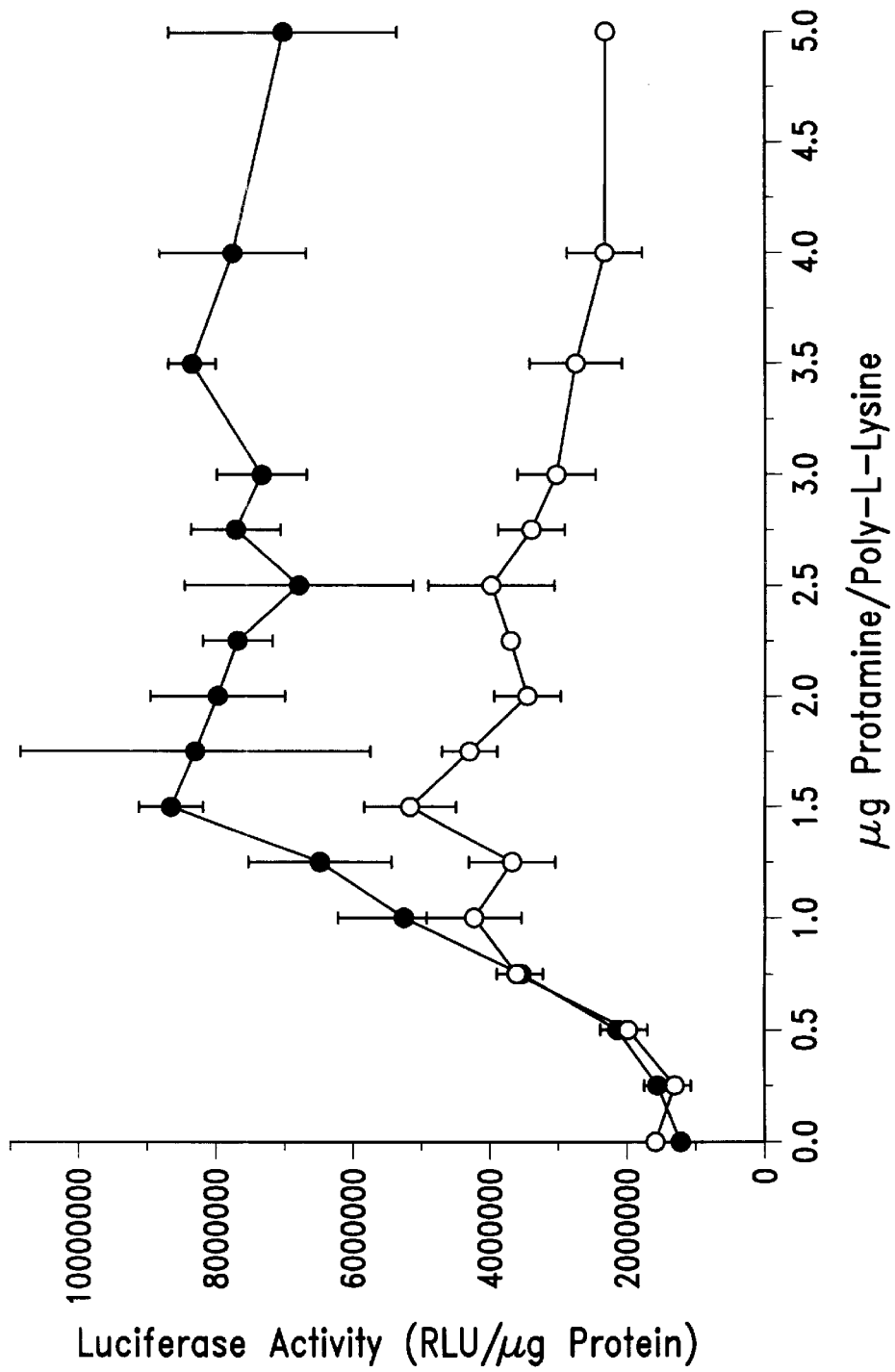
Figure 9:
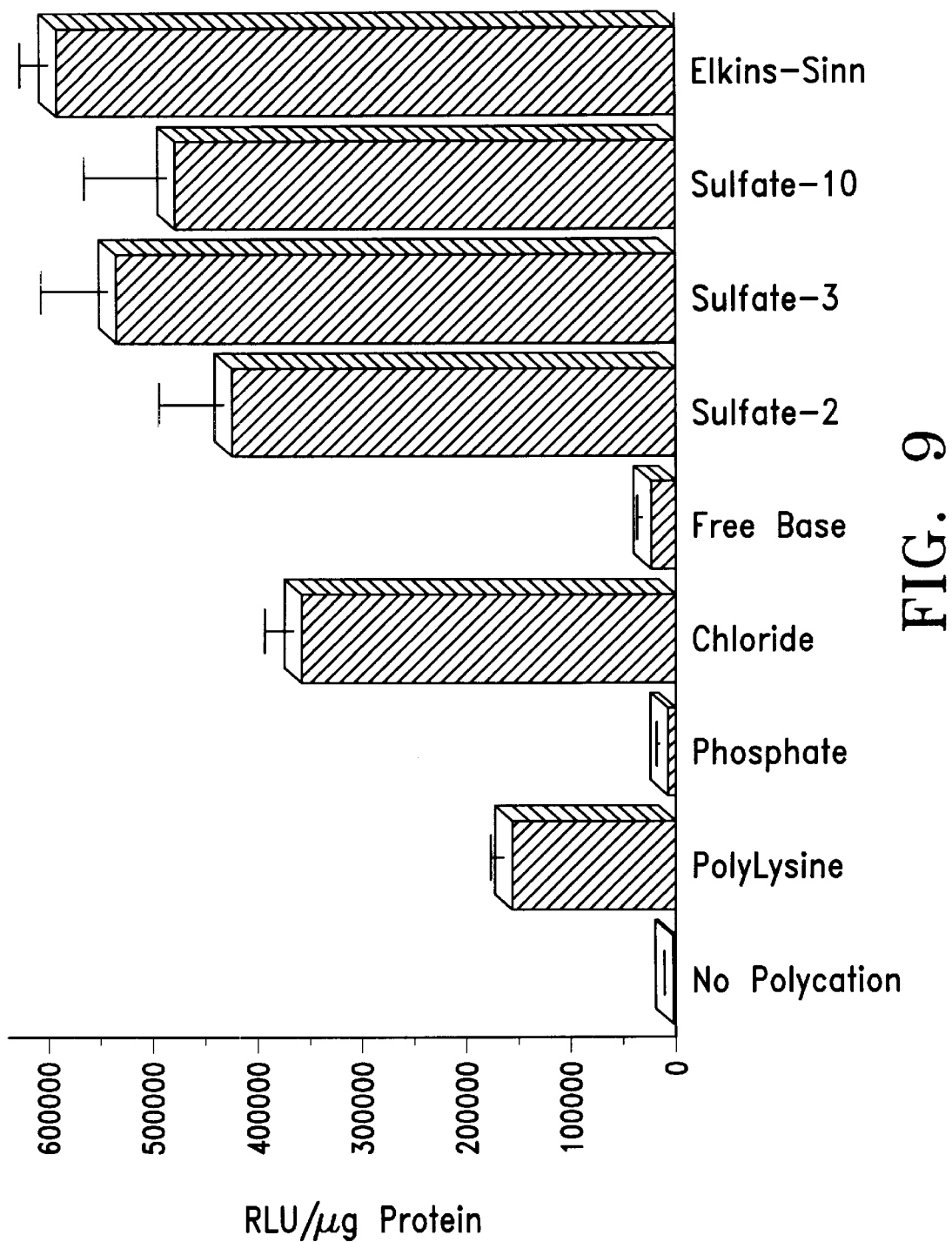
FIG. 9 shows the effect on transfection activity of different types of protamine where 2 μg of each indicated type of protamine or 1 μg poly-L-lysine were added to 1 μg of pUK-21 CMV LUC DNA prior to complexing with 7.5 nmol of DC-Chol liposomes per well. Transfection, luciferase, and protein assays were performed as described in Example 10 and each point represents the mean (with standard deviation) of four data points and are normalized to protein.

As shown in FIGS. 8A and 8B, increasing amounts of poly-L-Lysine resulted in an increase in transfection activity reaching a constant level of activity at 1 µg of poly-L-lysine per 1 µg of DNA.

Increasing amounts of Protamine Sulfate, USP also resulted in an increase in expression, reaching a constant level of expression at 2 µg of Protamine Sulfate, USP per 1 µg of DNA (see FIGS. 8A and 8B). However, in sharp contrast to the previously published report of Gao and Huang ((1996) Biochem., 35:1027–1036), in which transfection activity with protamine free base was consistently lower than that observed with poly-L-Lysine, the level of expression achieved with Protamine Sulfate, USP/DNA/liposome complexes was unexpectedly 4–5 fold higher than the levels seen with poly-L-lysine and 40-fold higher than that observed for DNA/liposome complexes without polycation.

Example 10
Effect of Different Types of Protamine on Transfection Activity

In order to further explore this unexpected difference in the ability of protamine free base and protamine sulfate USP to potentate transfection activity, the ability of various types of protamine to potentiate gene expression in CHO cells was compared to standard DNA/liposome complexes as well as complexes supplemented with poly-L-Lysine.

As shown in FIG. 9, the potentiation of gene expression by different types of protamine varied considerably with protamine phosphate and free base showing minimal if any increase in gene expression over that seen in the absence of any polycation while protamine sulfates showed a 3–5 fold increase in gene expression over poly-L-lysine and increased gene expression by 60-fold over background (DNA/lipid complex without a polycation (poly-L-lysine or protamine sulfate)). In addition, protamine chloride also showed an increase in gene expression over poly-L-lysine, albeit not as great an increase as that observed for protamine sulfates Example 11
Amino Acid Analysis of Various Types of Protamine In an effort to explain the large variation in transfection activity of the various protamines described above, the relative percentages of amino acid residues (i.e., amino acid composition) present in protamine phosphate, chloride, free base, sulfate (grade III), and sulfate USP (Lilly and Elkins-Sinn) were determined for each compound. The results of this analysis are presented in Table 5. Predicted values are calculated from a published sequence of salmon sperm (Warrant and Kim, (1978) Nature, 271:130–135).

TABLE 5

Amino Acid Composition of Various Salts of Protamine (expressed as percentage of composition)

| Amino Acid | Free Base | Phosphate | Chloride | Sulfate (Grade III) | Sulfate, USP (Lilly) | Sulfate, USP (Elkins-Sinn) | Predicted * |
|---|---|---|---|---|---|---|---|
| Aspartate | 0.23 | 0.55 | 0 | 0.12 | 0.50 | 0.03 | 0 |
| Threonine | 0.10 | 0.35 | 0 | 0 | 0 | 0 | 0 |
| Serine | 5.95 | 6.60 | 8.91 | 8.46 | 8.95 | 8.23 | 12.5 |
| Glutamate | 0.07 | 0.01 | 0 | 0 | 0.09 | 0 | 0 |
| Glycine | 6.69 | 7.07 | 7.04 | 6.56 | 7.30 | 6.36 | 6.25 |
| Alanine | 1.44 | 1.76 | 1.49 | 0.94 | 1.73 | 1.32 | 0 |
| Valine | 4.69 | 4.57 | 4.61 | 4.93 | 4.43 | 4.31 | 6.25 |
| Methionine | 0.56 | 0.77 | 0.70 | 0.64 | 0.75 | 0.64 | 0 |
| Isoleucine | 1.26 | 1.23 | 1.33 | 0.68 | 1.31 | 1.20 | 0 |
| Leucine | 0.17 | 0.20 | 0 | 0 | 0.22 | 0 | 0 |
| Histidine | 0.10 | 0.11 | 0 | 0 | 0 | 0 | 0 |
| Lysine | 8.14 | 8.84 | 1.49 | 0.47 | 0.21 | 0.23 | 0 |
| Arginine | 61.82 | 59.61 | 70.37 | 68.25 | 65.90 | 69.27 | 65.63 |
| Proline | 8.79 | 8.35 | 8.60 | 8.81 | 8.27 | 8.42 | 9.38 |

As can be seen, the amino acid composition of protamine free base is very similar to that of the protamine phosphate. Strong similarity in amino acid composition is also observed among the three different protamine sulfates and protamine chloride. Of particular interest are the differences in amino acid composition between the protamine sulfates and protamine chloride and the protamine free base and phosphate. The most striking difference is a 6–32 fold increase in lysine content in the phosphate and free base form of protamine relative to the sulfates and the chloride. An additional difference is a 1.5 fold increase in the amount of serine in the chloride and the sulfates relative to the phosphate and free base. Also observed is a decrease in the percentage of arginine present in the free base and phosphate in comparison to the sulfates and chloride. Of particular interest, the observed differences in lysine content correlate with the variations in activity observed in FIG. 9.

Of clinical interest, protamines are naturally occurring compounds which elicit rare, if any immune responses in the host and have been used clinically for several decades in insulin delivery systems whereas all current delivery systems utilize synthetic polymers having unknown safety profiles in humans.

Figure 10:
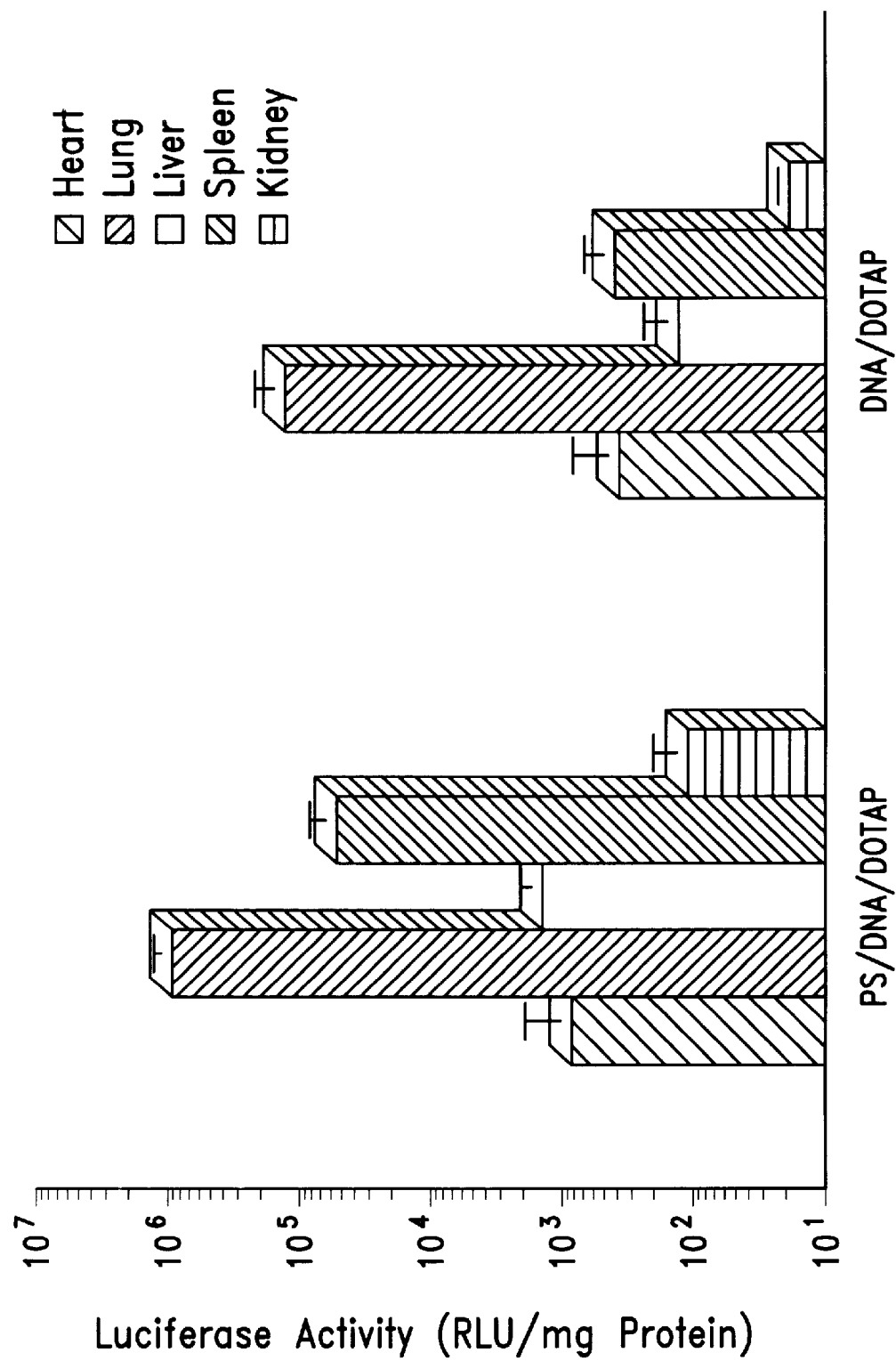
FIG. 10 shows two different formulations which were prepared by mixing pCMV-Luc DNA with DOTAP (25.38 μg/;μg DNA) or DNA with Protamine Sulfate, USP (PS) and complexing this mixture with DOTAP (0.8 μg PS/μg DNA/23.27 μg DOTAP). Dextrose was added to both formulations to make a final concentration of 5%, and were subsequently injected into mice (CD 1 female, 4–6 weeks old) through the tail vein (50 μg of DNA/mouse). Twenty-four hours following injection, the mice were sacrificed and the major organs collected. Tissues were homogenized in a lysis buffer, centrifuged at 14,000 g for 10 min and the supernatant was analyzed for luciferase activity and protein content. The results are expressed as relative light units (RLU) per mg of protein (n=3). No activity was found with DNA complexed with PS (0.8 μg PS/μg DNA) in the absence of DOTAP (data not shown). Complexation of DOTAP with DNA gave a variable level of expression, mainly in the lung. Inclusion of Protamine Sulfate, USP into the DNA/DOTAP complex resulted in a more consistent and higher level of gene expression.
Figure 11:
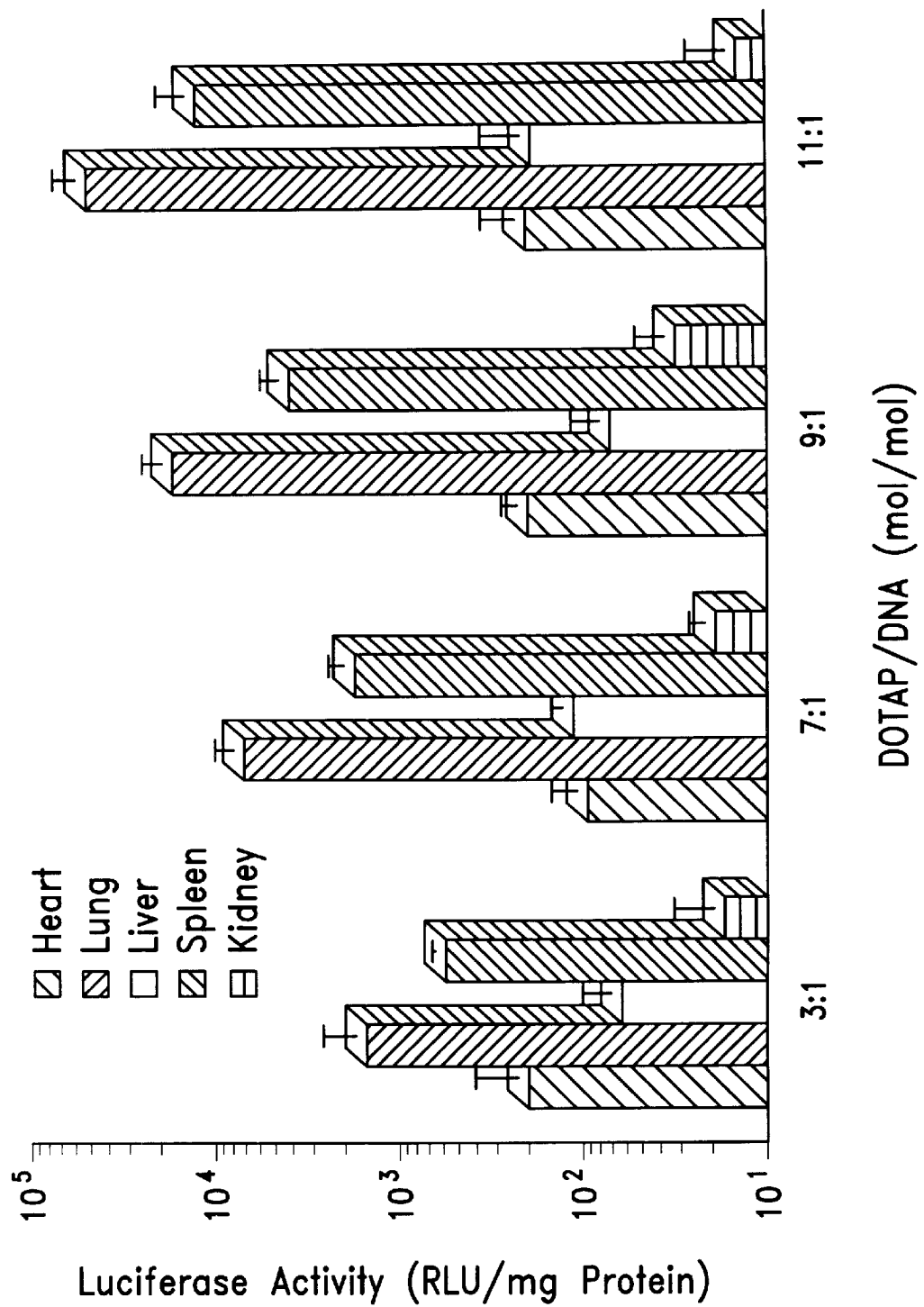
FIG. 11 shows in vivo gene expression of PS/DNA/DOTAP complexes as a function of DOTAP concentration. DNA was mixed with PS (0.8 μg PS/μg DNA) followed by complexation with increasing amounts of DOTAP. Injection of these complexes and assay of gene expression were performed as described in FIG. 10. The results indicate increasing amounts of DOTAP were associated with increases in gene expression in the lungs and spleen (n=3).
Figure 12:
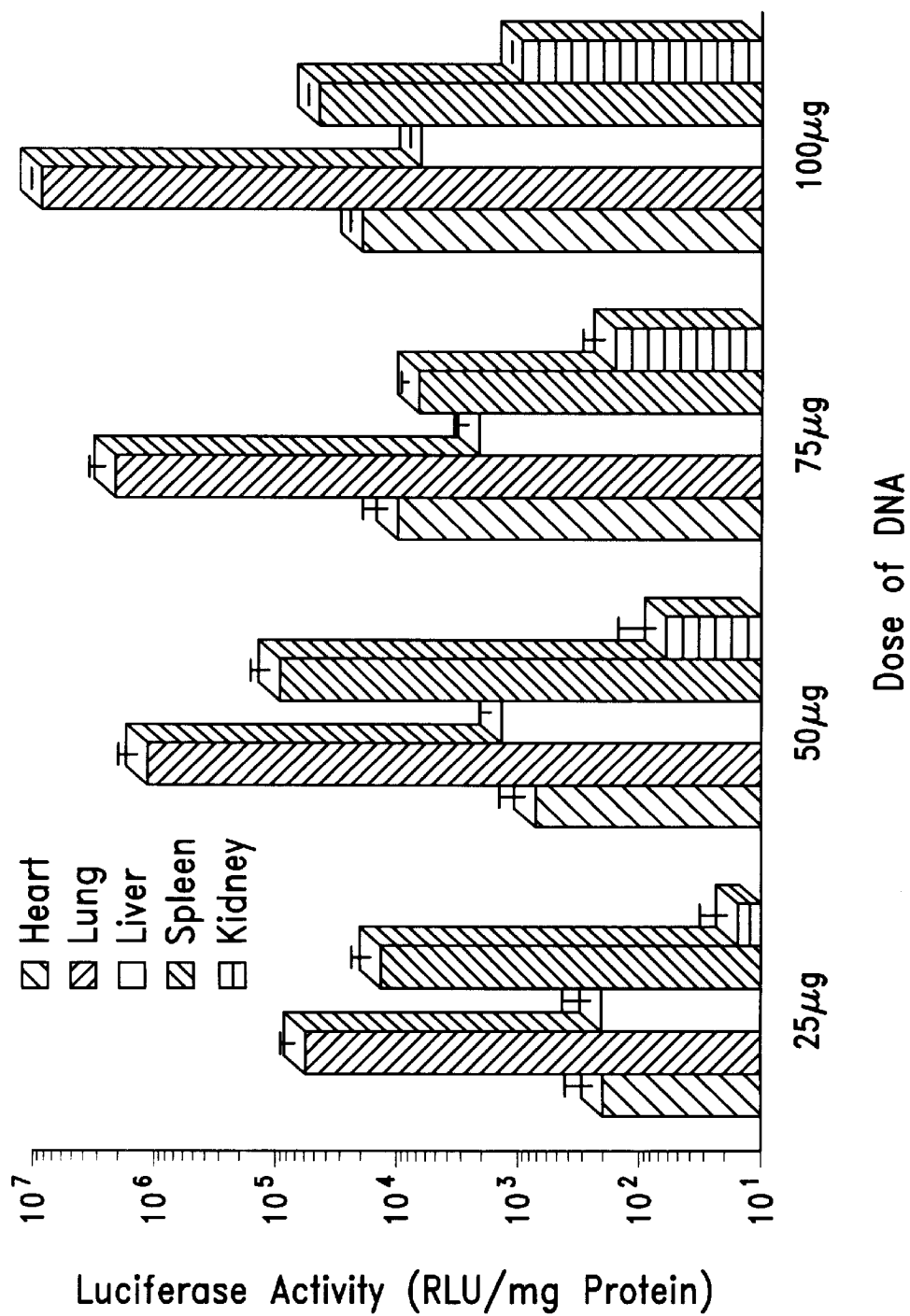
FIG. 12 shows in vivo gene expression of PS/DNA/DOTAP complexes as a function of the dose of the complex delivered. DNA was mixed with PS followed by complexation with DOTAP (0.8 μg PS/μg DNA/23.27 μg DOTAP) at increasing doses, as expressed by the dose of DNA. Increasing doses of the complex were injected into mice and gene expression was assayed 24 hours later (n=3). The results indicate increasing doses of the PS/DNA/DOTAP complex were associated with an increase in gene expression. However, at the dose above 75 μg (of DNA) per mouse, toxicity was noticed and one mouse died at a dose of 100 μg (of DNA).
Figure 13:
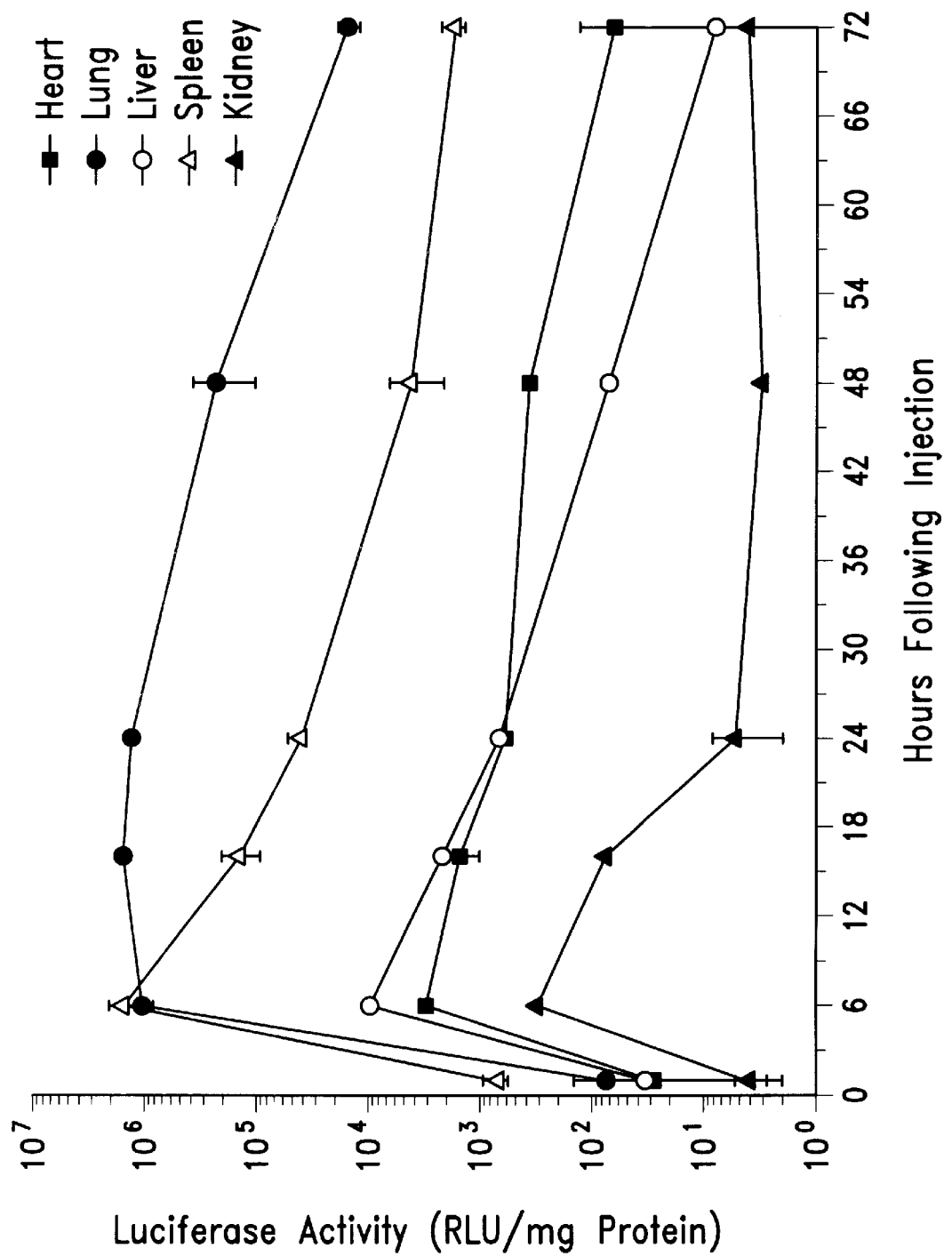
FIG. 13 shows in vivo gene expression of PS/DNA/DOTAP complexes as a function of time. PS/DNA/DOTAP complexes were prepared as described in FIG. 12 and were injected into mice at a DNA dose of 50 μg per mouse. At different times following injection, the mice were sacrificed and the major organs were assayed for gene expression (n=3). It can be seen that high levels of gene expression was observed in the lung as early as 6 hours following injection and persisted for 24 hours, declining thereafter. High levels of gene expression were also detected in the spleen 6 hours after injection but declined with time.

Example 12
In Vivo Transfection by DNA/Protamine Sulfate/Lipid Complexes Use of PS/DNA/liposome formulations in vivo has been demonstrated by administering various formulations intravenously to mice and assaying for reporter gene based on luciferase activity. A formulation containing PS/DNA/DOTAP (0.8 µg/1 µg/23.27 µg) in 5% dextrose has been shown to have a greater transfection activity than either PS/DNA (0.8 µg/1 µg) (data not shown) or complexes produced in the absence of PS (23.27 µg DOTA/µg DNA) (FIG. 10). Gene expression was highest in lung tissue compared to kidney, spleen, liver, and heart. In vivo luciferase activity was positively correlated with increasing concentrations of DOTAP and was maximal at a level of 11:1 (DOTAP/DNA mol/mol) (FIG. 11). Increasing the concentration of DNA also resulted in increased gene expression but was associated with some toxicity above a dose of 75 µg of DNA and the death of one mouse at a dose of 100 µg of DNA (FIG. 12). In vivo gene expression appeared to be maximal at 6 hours following injection and subsequently declined thereafter (FIG. 13).

Example 13
In Vitro Optimization of amounts of Protamine Sulfate, DNA, and DC-Chol Liposomes for Maximal Transfection.

Figure 14:
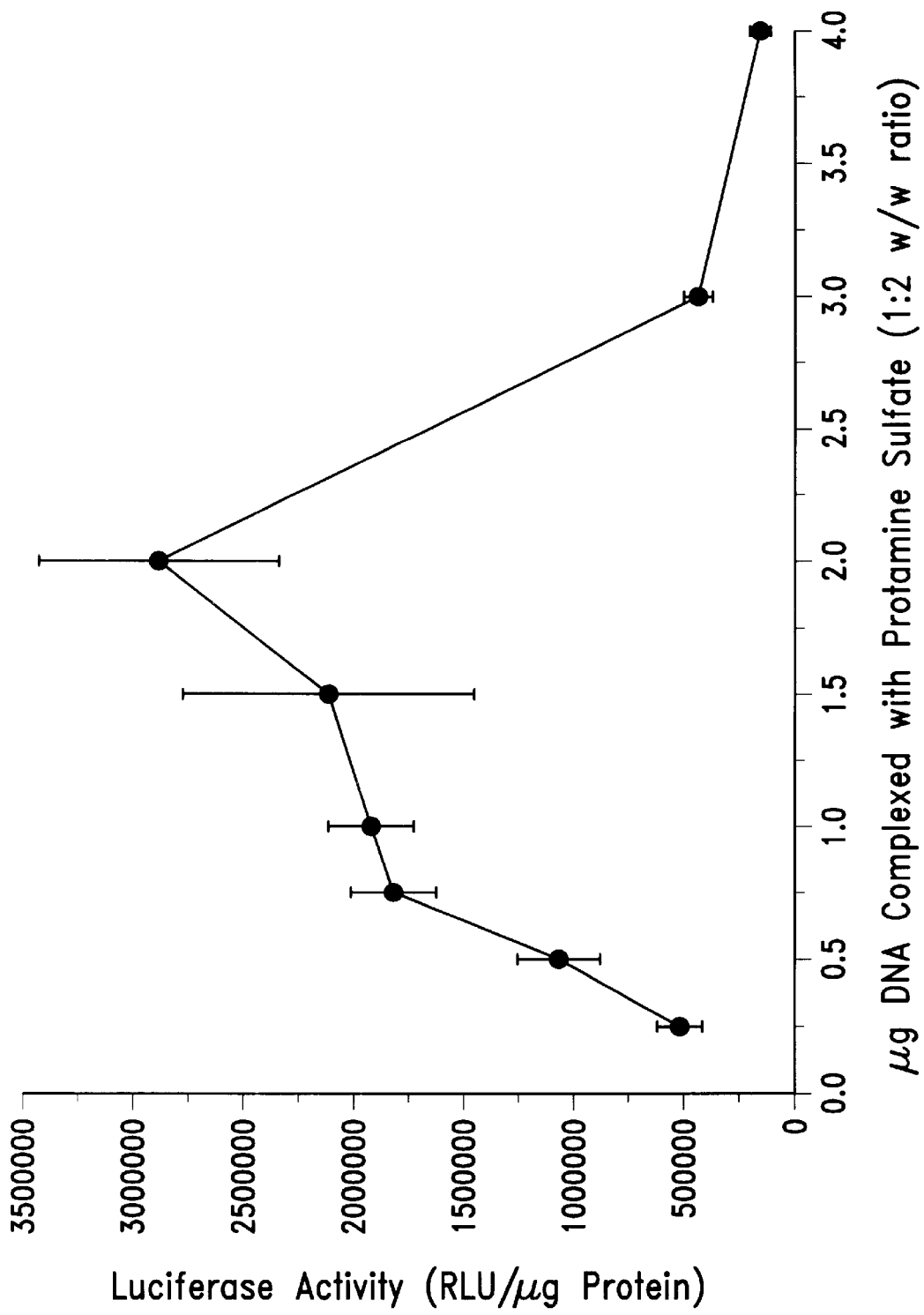
FIG. 14 shows the in vitro transfection activity of increasing amounts of PS/DNA (2:1 w/w ratio) at a fixed amount (7.5 nmol) of DC-Chol liposomes in CHO cells. Optimal activity was seen at a dose of 2 μg of DNA, 4 μg PS and 7.5 nmol of DC-Chol liposomes.

Optimization of the protamine sulfate/DNA/DC-Chol liposome complexes were examined in order to establish parameters for the complex formulation. As shown in FIGS. 8A and 8B, maximal activity was seen when 2 µg of protamine sulfate was complexed with 1 µg of DNA and 7.5 nmol of DC-Chol liposomes. In order to establish the optimal amount of DNA/Protamine sulfate which can be delivered by a fixed amount of DC-Chol liposomes, increasing amounts of DNA/PS (at a 1:2 w/w ratio) were complexed with 7.5 nmol of DC-Chol liposomes. As can be seen in FIG. 14, optimal transfection activity was achieved when 2 µg of DNA and 4 µg of PS were complexed with 7.5 nmol of DC-Chol liposomes.

Figure 15:
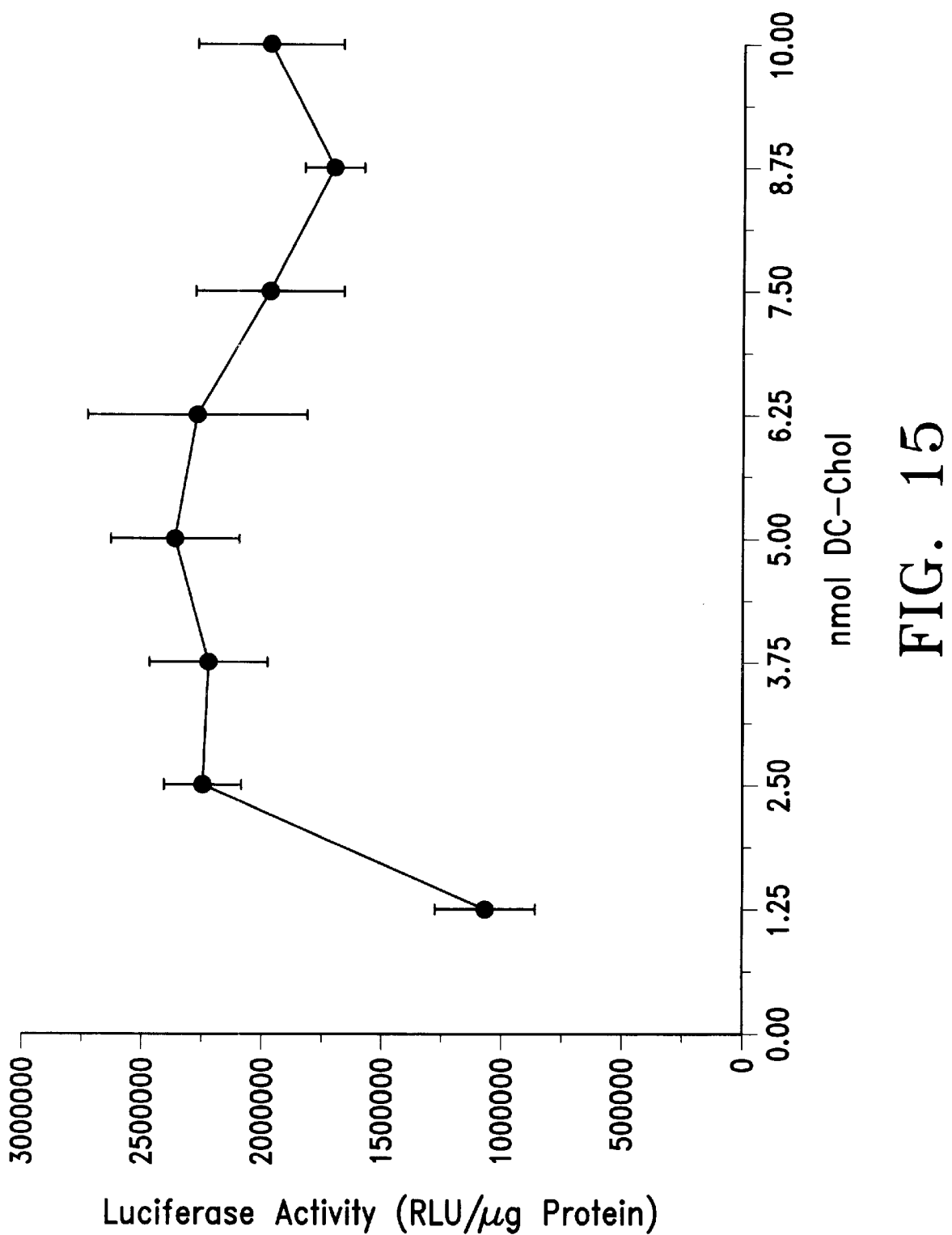
FIG. 15 shows the in vitro transfection activity of increasing amounts of DC-Chol liposomes at a fixed amount of PS/DNA (2 μg PS; 1 μg DNA) in CHO cells. Optimal activity was seen at 2.5 nmol of DC-Chol liposomes and remained constant thereafter, indicating that 2.5 nmol of DC-Chol liposomes was sufficient to adequately deliver 2 μg of PS and 1 μg of DNA.
Figure 16:
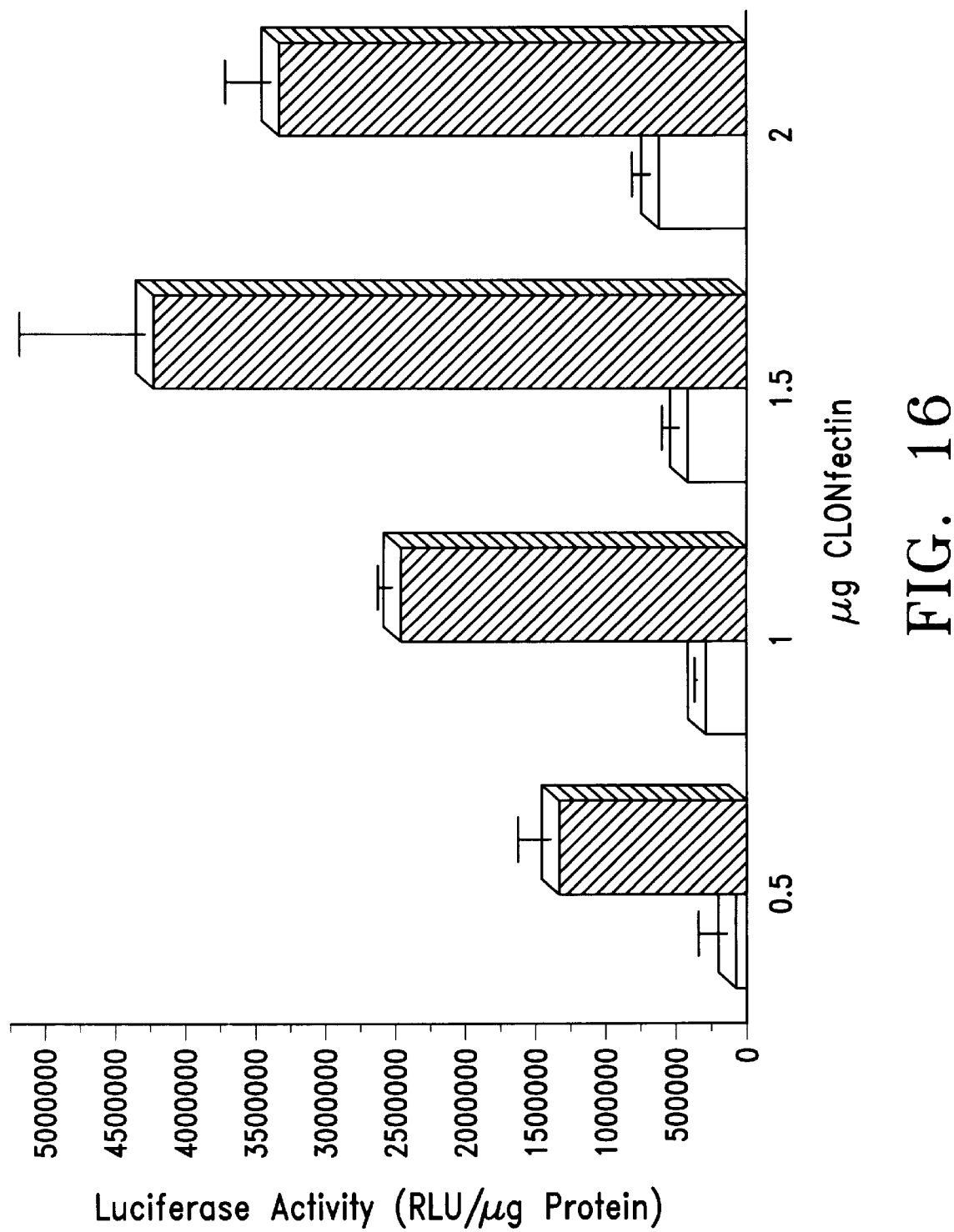
FIGS. 16–19 show the ability of PS to augment gene expression when complexed to DNA with Clonfectin (Clontech) (FIG. 16), DC-Chol liposomes (FIG. 17), Lipofectin (Gibco BRL) (FIG. 18), and DOTAP/DOPE (1:1 m/m) (Avanti Polar Lipids) (FIG. 19) formulations. CHO cells were transfected with various amounts of liposomes complexed with 1 μg of DNA with (■) or without (□) the inclusion of 2 μg of PS. With each liposome formulation, significant increases in transfection activity are noted in complexes containing PS when compared to complexes consisting of DNA alone with lipid. These results indicate that the increase in transfection activity is not limited to DC-Chol liposomes.

Having established that 2 µg of PS is required to optimally deliver 1 µg of DNA (FIGS. 8A and 8B), the amount of DC-Chol liposomes required to efficiently deliver this quantity of DNA/PS was determined. As shown in FIG. 15, using 1 µg of DNA complexed with 2 µg of PS, efficient delivery was established with as little as 2.5 nmol of DC-Chol liposomes. Prior experiments were performed at this DNA/PS ratio by using 7.5 nmol of DC-Chol liposomes. Since it is thought that cellular toxicity is a function of liposome concentration, it is preferential to use as minimal a dose of lipids as needed to deliver a specified quantity of genetic material. FIG. 16 suggests that as little as 2.5 nmol of DC-Chol liposomes is required to deliver a complex consisting of 1 µg of DNA and 2 µg of PS. The results of FIG. 15 suggest that quantities of 2 µg of DNA and 4 µg of PS can be delivered efficiently. This finding suggests that 2 µg of DNA complexed with 4 µg of PS would best be delivered by 5 nmol of DC-Chol liposomes.

Figure 17:
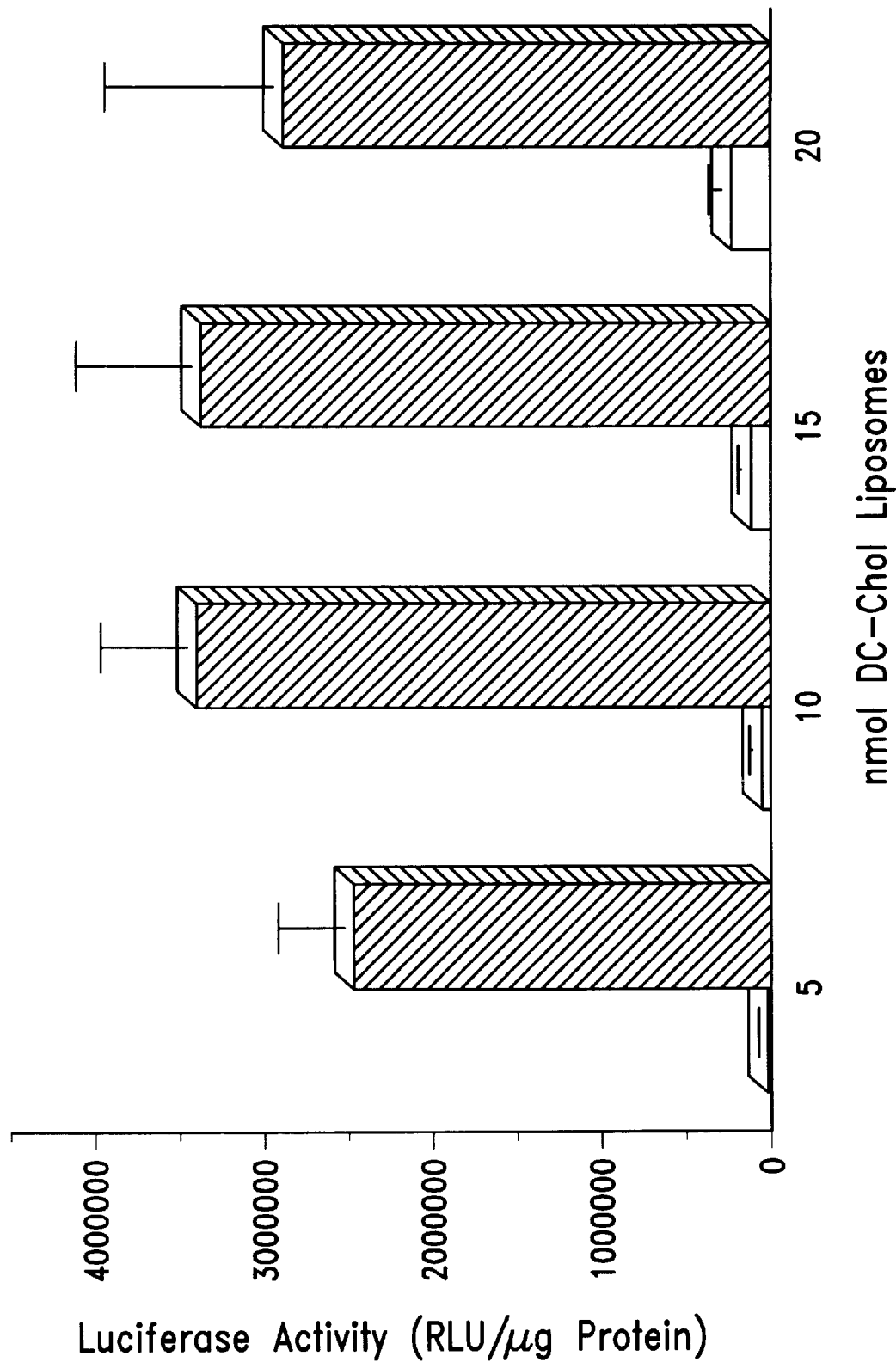
Figure 18:
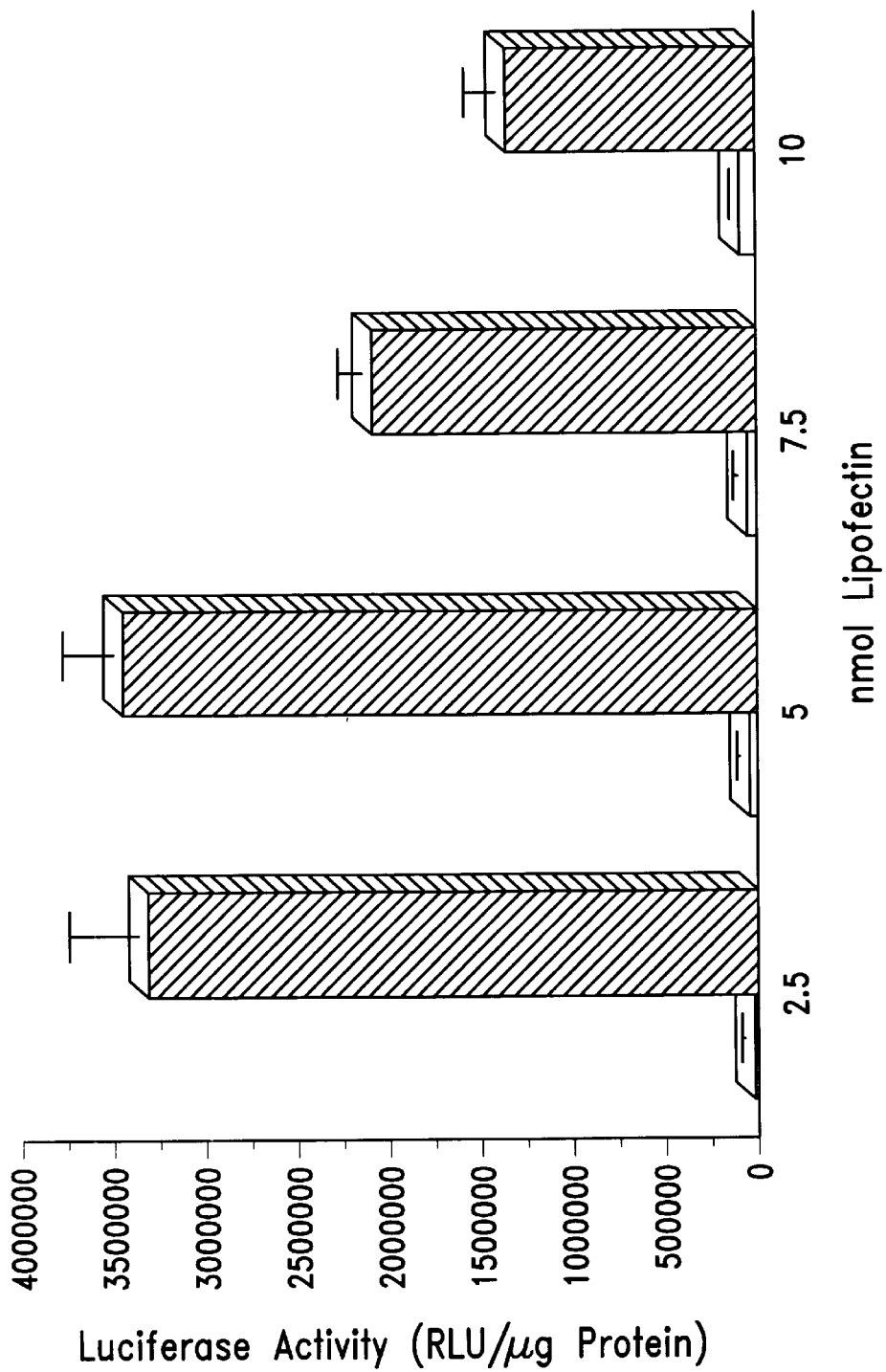
Figure 19:
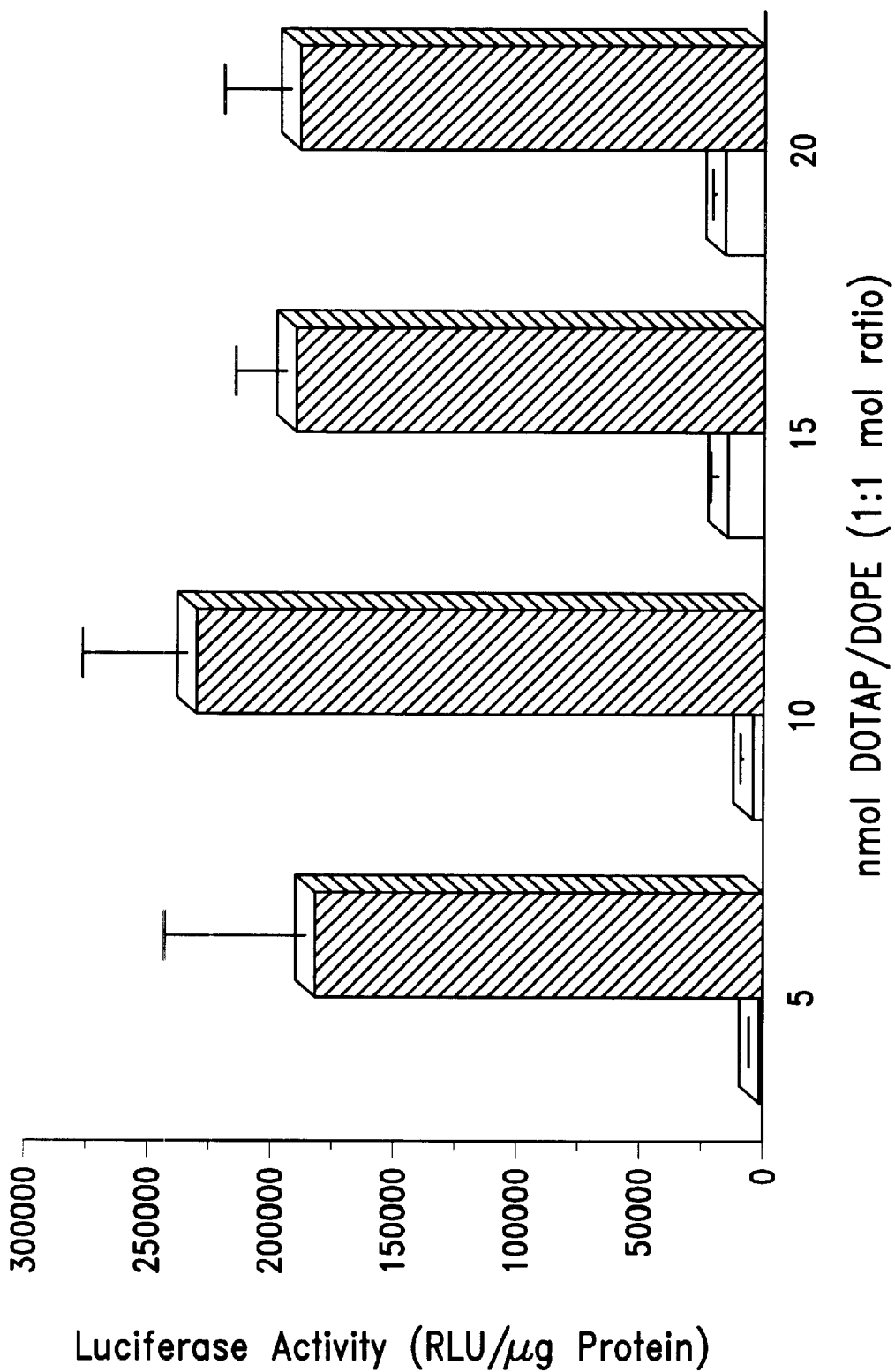

Example 14
The Ability of Protamine Sulfate to Increase the Transfection Activity of Several Different Cationic Liposome Formulations In Vitro Having established the ability of PS to augment the transfection activity of DC-Chol liposomes (FIGS. 8A and 8B), several other commercially available liposome formulations were also tested. FIG. 16 shows the ability of Clonfectin (Clontech) to transfect CHO cells with 1 µg of pUK 21 CMV LUC (□) and with a complex consisting of 2 µg of PS and 1 µg of DNA (■). The addition of PS results in a 5–20 fold increase in luciferase activity over the concentrations tested. FIG. 17 shows the ability of DC-Chol liposomes to transfect CHO cells with 1 µg of DNA (□) and with a complex consisting of 2 µg of PS and 1 µg of DNA (■). The addition of PS results in a 10–85 fold increase in luciferase activity over the concentrations tested. FIG. 18 shows the ability of Lipofectin (Gibco BRL) to transfect CHO cells with 1 µg of pUK 21 CMV LUC (□) and a complex consisting of 2 µg of PS and 1 µg of DNA (□). The addition of PS results in a 15–105 fold increase in luciferase activity over the concentrations tested. FIG. 19 shows the ability of DOTAP/DOPE (1:1 mol/mol) liposomes to transfect CHO cells with 1 µg of pUK 21 CMV LUC (□) and with complex consisting of 2 µg of PS and 1 µg of DNA (■). The addition of PS results in a 10–220 fold increase in luciferase activity over the concentrations tested.

While we have hereinbefore described a number of embodiments of this invention, it is apparent that the basic constructions can be altered to provide other embodiments which utilize the methods and devices of this invention. Therefore, it will be appreciated that the scope of this invention is defined by the claims appended hereto rather than by the specific embodiments which have been presented hereinbefore by way of example.

Example 15
Relationship Between Lipid:Protamine Sulfate:DNA Ratios and Average Particle Size A number of lipid:protamine sulfate:DNA formulations were made and analyzed to establish the relationship between Lipid:Protamine Sulfate:DNA ratios and particle size. Complexes were formed between PS and pCMV-Luc plasmid DNA in incremental ratios varying from 0:0 to 4:0. Aliquots of DC-Chol HCI/DOPE (Aronex) suspended in 10% dextrose were added to the PS/DNA complex to produce Lipid:DNA ratios from 1:1 to 10:1. The particle sizes of the resulting LPD complexes were taken at room temperature on a Malvern Zetasizer when the complexes were first formed (Day 0) and again after storage at 4° C. for 7 days. The data generated from this study are shown in FIG. 20.

The data from FIG. 20 indicate a correlation between Lipid:Protamine Sulfate:DNA ratios and particle size.

Particle sizes around 200 nm are preferable for coated pit internalization.

Example 16
In Vitro Transfection Efficiency of Different LPD Formulations on HeLa and SKOV-3 cells HeLa and SKOV-3 cells were transfected with different LPD formulations according to the protocol presented in the Materials and Methods section. Transfection efficiency was measured using the Luciferase Assay 48 hrs post transfection.

As depicted in FIG. 21, the addition of 2 µg Protamine Sulfate to a 1:1 lipid-DNA complex increases luciferase activity in HeLa cells by 500 fold. The addition of Protamine Sulfate to a 10:1 lipid-DNA complex to produce a 10:2:1 LPD formulation increases luciferase by 50 fold. No improvement in transfection activity is observed beyond a ratio of 2:1 Protamine:DNA.

FIG. 22 presents a comparative study of the transfection efficiency of SKOV-3 cells using LPD and DC-Chol delivery vehicles. The n value represents the number of individual experiments which were averaged for this data table. LPD formulations produced consistently higher luciferase activity than did the DC-Chol formulations, with the 15:2:1 LPD complex proving 8–10 fold more efficient that the best LD complex.

Example 17
Transfection of Mammalian Cells In Vivo

Nude mice between 6 and 12 weeks of age were inoculated intraperitoneally with 2×10$^6$ SKOV-3 human ovarian carcinoma cells in a total injection volume of 0.5 mls of PBS. After 6–7 weeks of tumor cell engraftment animals were injected with different formulations of pCMV-luc plasmid DNA and DNA/Lipid in a total volume of 1.0 ml (5% Dextrose final, isotonic solution). Animals were sacrificed 16 hours post formulation injection. Tumor nodules were removed and lysed. Protein concentrations were determined according to the Luciferase Assay described above.

FIG. 23 shows data comparing the in vivo transfection efficiency of vehicle plus naked DNA to following LPD formulations: 0:0:1, 0:2:1, 3:0:1, 3:2:1, 10:0:1, 10:2:1, 15:0:1 and 15:2:1. The RLU/mg values obtained for each individual mouse are denoted by circles, while the average RLU/mg values are shown as squares. Data show that the 15:2:1 LPD complex produced the highest average expression level of the formulations tested, yielding a 3–4 fold higher expression value.

Example 18
LPD E1A Survivability Study

Nude mice were injected intraperitoneally with 2×10$^6$ SKOV-3ip1 cells (a human ovarian carcinoma cell line selected as a subline from SKOV-3 due to its more rapid growth and higher HER2/neu expression). At five days post implantation, a treatment regimen involving delivery of the E1A expression plasmid comprising the Ad5 E1A gene with its native promoter (see, e.g., Mien-Chie Hung et al., U.S. Pat. No. 5,651,964). Animals were injected intraperitoneally on days 5, 6, and 7 with 1 ml of a 5% Dextrose vehicle comprising the formulations presented in FIG. 24: Group 1 animals were repeatedly injected with the 5% Dextrose vehicle only; Group 2 animals were repeatedly injected with the equivalent amount of DC-Chol/DOPE (6:4 ratio) and Protamine sulfate as one would find in the high dose 15:2:1 group but without the E1A expression plasmid present; Group 3 animals were repeatedly injected with 15 μg/dose of naked E1A expression plasmid, which was equivalent to the highest dose injected in formulated vehicles; Group 4 animals were repeatedly injected with 15 μg/dose of E1A expression plasmid compacted with Protamine sulfate at a ratio of 2 μg Protamine/1 μg DNA, which was equivalent to the highest dose injected in the formulated vehicles; Group 14 animals were repeatedly injected with a 1.5 μg/dose 15:2:1 LPD formulation; Group 15 animals were repeatedly injected with a 5 μg/dose 15:2:1 LPD formulation; Group 16 animals were repeatedly injected with a 15 μg/dose LPD formulation. Animals were subsequently injected once a week with the same formulation for the time listed on the X axis. Animals either survived, died due to tumor burden, or were sacrificed prior to death if death was imminent.

Figure 24:
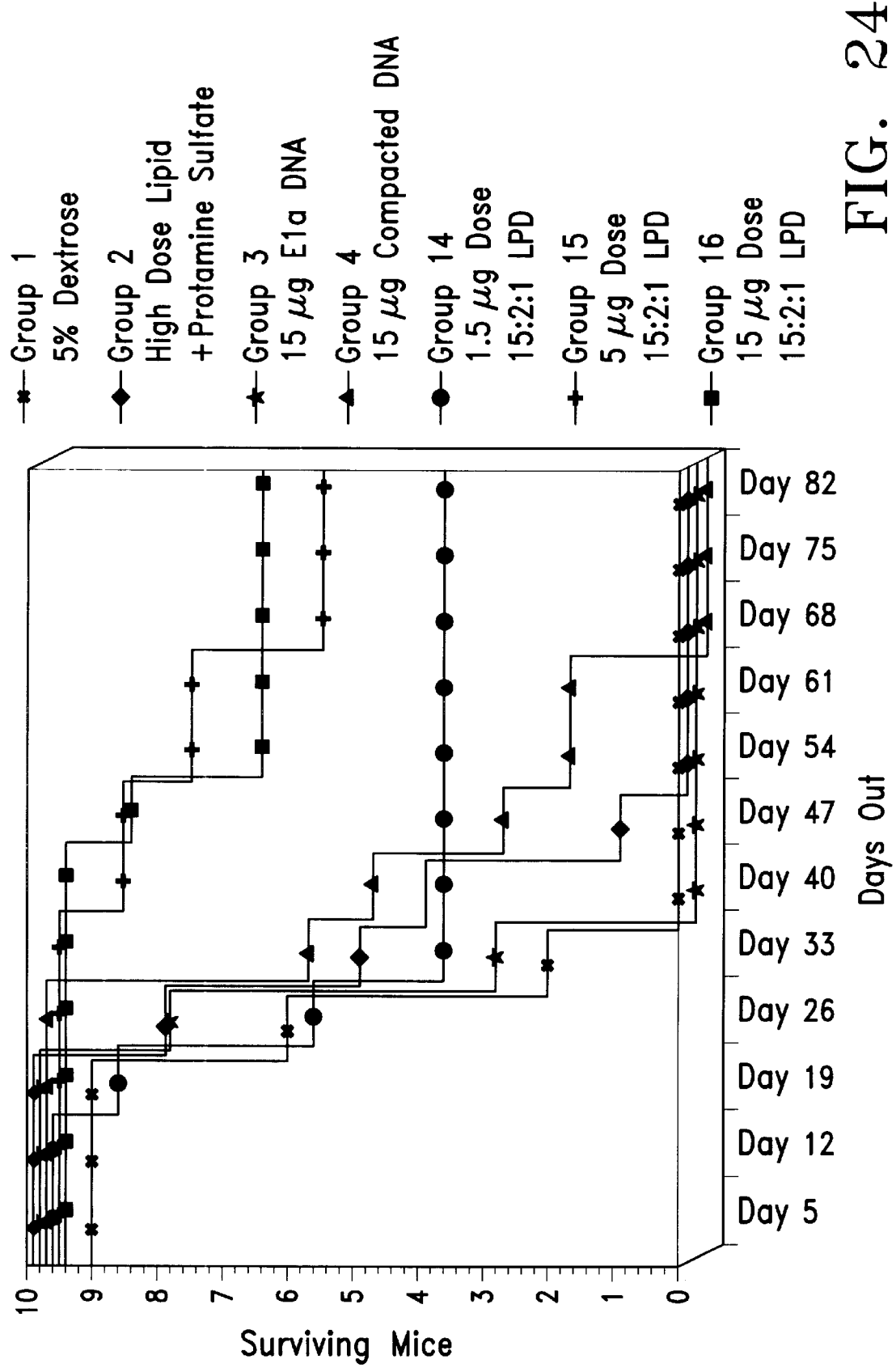
FIG. 24 shows a dose response graph for the treatment of Nude mice injected intraperitoneally with $2\times10^6$ SKOV-3ip1 cells at Day 0. On Day 5 mice were injected with with different L:P:D formulations comprising an E1A expression plasmid. Group 1 animals were repeatedly injected with the 5% Dextrose vehicle only; Group 2 animals were repeatedly injected with the equivalent amount of DC-Chol/DOPE (6:4 mol:mol ratio) and Protamine sulfate as one would find in the high dose 15:2:1 group but without the E1A expression plasmid present; Group 3 animals were repeatedly injected with 15 μg/dose of naked E1A expression plasmid, which was equivalent to the highest dose injected in formulated vehicles; Group 4 animals were repeatedly injected with 15 μg/dose of E1A expression plasmid compacted with Protamine sulfate at a ratio of 2 μg Protamine/1 μg DNA, which was equivalent to the highest dose injected in the formulated vehicles; Group 14 animals were repeatedly injected with a 1.5 μg/dose 15:2:1 LPD formulation; Group 15 animals were repeatedly injected with a 5 μg/dose 15:2:1 LPD formulation; Group 16 animals were repeatedly injected with a 15 μg/dose LPD formulation. The time course of the experiment in days is shown on the X axis. The number of surviving mice is shown on the Y axis.

FIG. 24 shows that DNA must be formulated in a lipid vehicle to work properly upon intraperitoneal injection (Groups 3 and 4). The data further demonstrate a positive correlation between the dose of E1A given as a lipid formulation and the mouse survival rate (Groups 14, 15 and 16).

We claim:

1. A drug/lipid/polycationic polypeptide salt complex comprising a drug, at least one lipid species, and at least one polycationic polypeptide salt.

2. The complex of claim 1, comprising a drug, at least one lipid species, and at least one polycationic polypeptide salt in a ratio such that the complex has a positive charge excess of lipid and polycationic polypeptide to drug.

3. The complex of claim 1 wherein, in the polycationic polypeptide salt, arginine residues constitute at least about 30% of the amino acid residues, and lysine residues constitute less than about 5% of the amino acid residues of the polypeptide.

4. A nucleic acid/lipid/polycationic polypeptide complex comprising a nucleic acid, at least one lipid species, and at least one polycationic polypeptide in a ratio such that the complex has a positive charge excess of lipid and polycationic polypeptide to nucleic acid, wherein, in the polycationic polypeptide, arginine residues constitute about 65 to 75% of the amino acid residues, and lysine residues constitute about 0 to 3% of the amino acid residues of the polypeptide.

5. The complex of claim 1, wherein the polycationic polypeptide salt is a sulfate salt.

6. The complex of claim 1, wherein the polypeptide salt comprises an ion having two negative charges.

7. The complex of claim 1, wherein the polycationic polypeptide salt is a protamine sulfate.

8. The complex of claim 1, wherein the drug is a nucleic acid.

9. The complex of claim 8, wherein the nucleic acid comprises an E1A gene.

10. The complex of claim 1, wherein the lipid is a cationic lipid.

11. The complex of claim 1, wherein the lipid is 3β[N-(N', N'-dimethylaminoethane)-carbamoyl]cholesterol (DC-Chol).

12. The complex of claim 1, wherein the polypeptide is from about 20 to about 100 amino acids in length.

13. The complex of claim 1, wherein the complex further comprises a neutral phospholipid species.

14. The complex of claim 13, wherein the lipid is 3β[N-(N', N'-dimethylaminoethane)-carbamoyl]cholesterol (DC-Chol), the neutral phospholipid is dioleoyl phosphatidylethanolamine (DOPE), the polycationic polypeptide salt is a protamine sulfate, and the drug comprises a nucleic acid.

15. The complex of claim 14, wherein the nucleic acid comprises an E1A gene.

16. The complex of claim 8, wherein the ratio of the nucleic acid:lipid:polycationic polypeptide salt is about 1 μg/0.1 nmol/0.01 μg to about 1 μg/200 nmol/100 μg.

17. The complex of claim 1, wherein the complex has a diameter of less than about 400 nm.

18. The complex of claim 1, wherein the complex is shielded to enhance the circulatory half-life of the complex.

19. The complex of claim 1, further comprising a lipophilic surfactant.

20. The complex of claim 1, further comprising a compound comprising polyethylene glycol moieties.

21. The complex of claim 1, wherein the complex is shielded to enhance the circulatory half-life of the complex.

22. The complex of claim 1, further comprising a lipophilic surfactant.

23. The complex of claim 1, further comprising a compound comprising polyethylene glycol moieties.

24. A complex comprising drug, at least one lipid species, and at least one polycationic polypeptide salt, wherein the polycationic polypeptide salt is a protamine sulfate.

25. A method for producing a drug/lipid/polycationic polypeptide salt complex of claim 1, the method comprising combining the drug, the lipid and the polycationic polypeptide salt to form the complex.

26. The method of claim 25, wherein the drug, lipid and polycationic polypeptide salt are mixed in a ratio of about 1 μg/0.1 nmol/0.01 μg to 1 μg/200 nmol/100 μg.

27. The method of claim 25, wherein the lipid is a cationic lipid.

28. The method of claim 27, wherein the cationic lipid is 3β[N-(N', N'-dimethylaminoethane)-carbamoyl]cholesterol (DC-Chol).

29. The method of claim 25, wherein the complex further comprises a neutral phospholipid.

30. The method of claim 29, wherein the lipid is 3β[N-(N', N'-dimethylaminoethane)-carbamoyl]cholesterol (DC-Chol), the neutral phospholipid is dioleoyl phosphatidylethanolamine (DOPE), the drug is a nucleic acid and the polycationic polypeptide salt is a protamine sulfate.

31. The method of claim 25, wherein the drug is a nucleic acid.

32. The method of claim 25, wherein the polycationic polypeptide salt is a protamine sulfate.

33. The method of claim 25, wherein the complex has a diameter of less than about 400 nm.

34. The method of claim 33, wherein the diameter of the complex remains substantially unchanged for up to one year in storage.

35. A method for delivering drug to cells comprising contacting the cells with the complex of claim 1.

36. A method for delivering drug to cells comprising contacting the cells with the complex of claim 24.

37. The method of claim 35, wherein the cells are contacted with the complex in vivo, the method comprising administering the complex to an animal or human in an amount effective to deliver the drug into the cells of the animal or the human.

38. The method of claim 37, wherein the lipid is 3β[N-(N', N'-dimethylaminoethane)-carbamoyl]cholesterol (DC-Chol).

39. The method of claim 37, wherein the polycationic polypeptide salt is a protamine sulfate.

40. The method of claim 37, wherein the drug is a nucleic acid.

41. The method of claim 37, wherein the drug comprises an E1A gene, the lipid is 3β[N-(N', N'-dimethylaminoethane)-carbamoyl]cholesterol (DC-Chol), and the polycationic polypeptide salt is a protamine sulfate.

42. The method of claim 36, wherein the cells are contacted with the complex in vivo, the method comprising administering the complex to an animal or human in an amount effective to deliver the drug into the cells of the animal or the human.

43. The method of claim 42, wherein the lipid is 3β[N-(N', N'-dimethylaminoethane)-carbamoyl]cholesterol (DC-Chol).

44. The method of claim 42, wherein the drug is a nucleic acid.

45. The method of claim 25, further comprising purifying the complex by a method selected from the group consisting of centrifugation, chromatography, filtration and phase partition.

46. A method of delivering a nucleic acid to a cell, the method comprising contacting the cell with a complex of claim 4.

* * * * *

UNITED STATES PATENT AND TRADEMARK OFFICE
CERTIFICATE OF CORRECTION

PATENT NO. : 6,008,202
DATED : December 28, 1999
INVENTOR(S) : Leaf Huang, et. al.

It is certified that error appears in the above-indentified patent and that said Letters Patent is hereby corrected as shown below:

In Column 1, line 13, please insert:

--STATEMENT OF RIGHTS TO INVENTIONS MADE UNDER FEDERALLY SPONSORED RESEARCH

This invention was made with Government support under Grant No. DK44935, awarded by the National Institutes of Health. The Government has certain rights in this invention."--

Signed and Sealed this

Thirteenth Day of March, 2001

NICHOLAS P. GODICI

*Attest:*

*Attesting Officer*   *Acting Director of the United States Patent and Trademark Office*